(12) United States Patent
Donaduzzi et al.

(10) Patent No.: US 11,389,423 B2
(45) Date of Patent: Jul. 19, 2022

(54) PHARMACEUTICAL COMPOSITION, EXCIPIENT FOR THE COMPOSITION AND USE OF THE COMPOSITION

(71) Applicants: Prati, Donaduzzi & Cia Ltda, Toledo (BR); Universidade De São Paulo, São Paulo (BR)

(72) Inventors: Luiz Donaduzzi, Toledo (BR); Carmen Maria Donaduzzi, Toledo (BR); Liberato Brum Junior, Toledo (BR); Patricia Moura Da Rosa Zimmerman, Toledo (BR); Emanuelle Webler, Toledo (BR); Leticia Mello Rechia, Toledo (BR); José Alexandre Crippa, Ribeirão Preto (BR); Jaime Eduardo Cecilio Hallak, Ribeirão Preto (BR); Antonio Waldo Zuardi, Ribeirão Preto (BR); Francisco Silveira Guimarães, Ribeirão Preto (BR); Alline Cristina De Campos, Ribeirão Preto (BR); Vitor Tumas, Ribeirão Preto (BR); Elaine Aparecida Del Bel Belluz Guimarães, Ribeirão Preto (BR)

(73) Assignees: Prati, Donaduzzi & Cia Ltda, Toledo (BR); Universidade De São Paulo, São Paulo (BR)

(*) Notice: Subject to any disclaimer, the term of this patent is extended or adjusted under 35 U.S.C. 154(b) by 19 days.

(21) Appl. No.: 16/967,334

(22) PCT Filed: Feb. 11, 2019

(86) PCT No.: PCT/BR2019/050040
§ 371 (c)(1),
(2) Date: Aug. 4, 2020

(87) PCT Pub. No.: WO2019/153064
PCT Pub. Date: Aug. 15, 2019

(65) Prior Publication Data
US 2020/0368197 A1   Nov. 26, 2020

(30) Foreign Application Priority Data
Feb. 9, 2018 (BR) .......................... 102018002843-0

(51) Int. Cl.
| | |
|---|---|
| *A61K 31/352* | (2006.01) |
| *A61K 31/05* | (2006.01) |
| *A61K 47/44* | (2017.01) |
| *A61P 25/28* | (2006.01) |
| *A61P 25/08* | (2006.01) |
| *A61P 25/16* | (2006.01) |
| *A61K 9/00* | (2006.01) |

(52) U.S. Cl.
CPC ............ *A61K 31/352* (2013.01); *A61K 31/05* (2013.01); *A61K 47/44* (2013.01); *A61P 25/08* (2018.01); *A61P 25/16* (2018.01); *A61P 25/28* (2018.01); *A61K 9/0053* (2013.01)

(58) Field of Classification Search
CPC ...... A61K 31/352; A61K 31/05; A61K 47/44; A61K 9/0053; A61P 25/28; A61P 25/08; A61P 25/16
See application file for complete search history.

(56) References Cited

U.S. PATENT DOCUMENTS

2016/0338974 A1* 11/2016 Aung-Din ............ A61K 31/433

FOREIGN PATENT DOCUMENTS

| WO | 2017045053 A1 | 3/2017 |
| WO | 2017204986 A1 | 11/2017 |
| WO | 2018011798 A1 | 1/2018 |

OTHER PUBLICATIONS

Celorrio, M. et al., GPR55: A therapeutic target for Parkinson's disease?, Neuropharmacology, v. 125, p. 319-332 (2017).
Bailey, K. et al., D. Distinction of Synthetic Cannabidiol, Cannabichromene, and Cannabivarin by GLC Using On-Column Methylation, J. Pharma. Sci., v. 64, n. 10, p. 1719-1720 (1975).
Turner, C.E. et al., Constituents of *Cannabis sativa* L. IX: Stability of Synthetic and Naturally Occurring Cannabinoids in Chloroform, J. Pharma. Sci., v. 64, n. 2, p. 357-359 (1975).
Mechoulam, R. et al., A total synthesis of dl-delta1-tetrahydrocannabinol, the active constituent of hashish, J. Am. Chem. Soc., v. 87, n. 14, p. 3273-3275 (1965).
Petrzilka, T. et al., Synthese con Haschisch-Inhaltsstoffen, 4 Mitteilung, Helvetica Chimica Acta, v. 52, fasc. 4, p. 1102-1134 (1969).
Ballerini, E. et al., High Pressure Diels-Alder Approach to Hydroxy-Substituted 6a-Cyano-tetrahydro-6H-benzo[c]chromen-6-ones: A Route to delta6-Cis-Cannabidiol, J. Org. Chem., v. 74, n. 11, p. 4311-4317 (2009).

(Continued)

*Primary Examiner* — Michael P Cohen
(74) *Attorney, Agent, or Firm* — Laurence P. Colton; Smith Tempel Blaha LLC

(57) ABSTRACT

A pharmaceutical composition containing synthetic Cannabidiol and its use in obtaining a medication for the treatment of neurological disorders, as well as the main excipients used in the production process, in addition to its small, medium, and large-scale preparation process. The use of the composition for the treatment of neurological disorders in human or animal populations, in particular in the treatment of Parkinson's disease, in the range of 300 to 850 mg/day or at daily doses of 100 to 1750 mg for neuroprotective action.

4 Claims, 16 Drawing Sheets

(56) References Cited

OTHER PUBLICATIONS

Bisogno, T. et al., Molecular targets for cannabidiol and its synthetic analogues: effect on vanilloid VR1 receptors and on the cellular uptake and enzymatic hydrolysis of anandamide, Brit. J. Pharma., v. 134, p. 845-852 (2001).

* cited by examiner

| Parameters | Placebo (8h) | | CBD 1 g/kg p.o. (8h) | | CBD 1 g/kg i.p. (8h) | | CBD 2 g/kg p.o. (8h) | | CBD 2 g/kg i.p. (8h) | |
|---|---|---|---|---|---|---|---|---|---|---|
| | Male | Female | Male | Female | Male | Female | Male | Female | Male | Female |
| Food | Normal | Normal | Normal | Normal | Normal | Normal | Normal | Normal | Normal | Normal |
| Aggressivity | Absent | Absent | Absent | Absent | Absent | Absent | Absent | Absent | Absent | Absent |
| Vision | Normal | Normal | Normal | Normal | Normal | Normal | Normal | Normal | Normal | Normal |
| Hearing | Normal | Normal | Normal | Normal | Normal | Normal | Normal | Normal | Normal | Normal |
| Convulsions | Absent | Absent | Absent | Absent | Absent | Absent | Absent | Absent | Absent | Absent |
| Salivation | Absent | Absent | Absent | Absent | Absent | Absent | Absent | Absent | Absent | Absent |
| Activity | Normal | Normal | Normal | Normal | Normal | Normal | Normal | Normal | Normal | Normal |
| Breathing | Normal | Normal | Normal | Normal | Normal | Normal | Normal | Normal | Normal | Normal |
| Heart rate | Normal | Normal | Normal | Normal | Normal | Normal | Normal | Normal | Normal | Normal |
| Diarrhea | Absent | Absent | Absent | Absent | Absent | Absent | Absent | Absent | Absent | Absent |
| Coma | Absent | Absent | Absent | Absent | Absent | Absent | Absent | Absent | Absent | Absent |
| Tissue injury | Absent | Absent | Absent | Absent | Absent | Absent | Absent | Absent | Absent | Absent |

Figure 1

| Parameters | Placebo (8h) | | CBD 1 g/kg p.o. (8h) | | CBD 1 g/kg i.p. (8h) | | CBD 2 g/kg p.o. (8h) | | CBD 2 g/kg i.p. (8h) | |
|---|---|---|---|---|---|---|---|---|---|---|
| | Male | Female | Male | Female | Male | Female | Male | Female | Male | Female |
| Food | Normal | Normal | Normal | Normal | Normal | Normal | Normal | Normal | Normal | Normal |
| Aggressivity | Absent | Absent | Absent | Absent | Absent | Absent | Absent | Absent | Absent | Absent |
| Vision | Normal | Normal | Normal | Normal | Normal | Normal | Normal | Normal | Normal | Normal |
| Hearing | Normal | Normal | Normal | Normal | Normal | Normal | Normal | Normal | Normal | Normal |
| Convulsions | Absent | Absent | Absent | Absent | Absent | Absent | Absent | Absent | Absent | Absent |
| Salivation | Absent | Absent | Absent | Absent | Absent | Absent | Absent | Absent | Absent | Absent |
| Activity | Normal | Normal | Normal | Normal | Normal | Normal | Normal | Normal | Normal | Normal |
| Breathing | Normal | Normal | Normal | Normal | Normal | Normal | Normal | Normal | Normal | Normal |
| Heart rate | Normal | Normal | Normal | Normal | Normal | Normal | Normal | Normal | Normal | Normal |
| Diarrhea | Absent | Absent | Absent | Absent | Absent | Absent | Absent | Absent | Absent | Absent |
| Coma | Absent | Absent | Absent | Absent | Absent | Absent | Absent | Absent | Absent | Absent |
| Tissue injury | Absent | Absent | Absent | Absent | Absent | Absent | Absent | Absent | Absent | Absent |

Figure 2

| Organ | Placebo | | CBD 1 g/kg p.o. | | CBD 1 g/kg i.p. | | CBD 2 g/kg p.o. | | CBD 2 g/kg i.p. | |
|---|---|---|---|---|---|---|---|---|---|---|
| | Male | Female | Male | Female | Male | Female | Male | Female | Male | Female |
| Body weight (g) | 389±17 | 210±10 | 397±21 | 201±7 | 391±14 | 203±9 | 401±19 | 207±8 | 397±19 | 199±10 |
| Relative weight (%) | | | | | | | | | | |
| Liver | 2.5±0.11 | 3.3±0.08 | 2.8±0.10 | 3.5±0.12 | 2.5±0.09 | 3.1±0.14 | 3.0±0.38 | 3.6±0.09 | 2.8±0.38 | 3.5±0.09 |
| Kidneys | 0.6±0.08 | 0.6±0.02 | 0.5±0.07 | 0.7±0.01 | 0.6±0.05 | 0.6±0.03 | 0.6±0.06 | 0.6±0.02 | 0.6±0.06 | 0.7±0.02 |
| Spleen | 0.1±0.02 | 0.2±0.01 | 0.1±0.05 | 0.2±0.01 | 0.1±0.02 | 0.2±0.05 | 0.1±0.02 | 0.2±0.01 | 0.1±0.02 | 0.2±0.01 |
| Absolut weight (g) | | | | | | | | | | |
| Liver | 10±0.69 | 7.0±0.32 | 11±0.70 | 7.0±0.28 | 10±0.59 | 6.4±0.64 | 12±1.90 | 7.4±0.35 | 11±1.80 | 7.1±0.32 |
| Kidneys | 2.2±0.13 | 1.3±0.04 | 2.2±0.15 | 1.4±0.09 | 2.3±0.11 | 1.2±0.09 | 2.4±0.12 | 1.2±0.04 | 2.4±0.13 | 1.3±0.31 |
| Spleen | 0.4±0.03 | 0.5±0.01 | 0.5±0.04 | 0.5±0.04 | 0.5±0.03 | 0.4±0.03 | 0.5±0.02 | 0.5±0.02 | 0.5±0.02 | 0.5±0.03 |

Figure 3

| Organ | Placebo | | CBD 1 g/kg p.o. | | CBD 1 g/Kg i.p. | | CBD 2 g/kg p.o. | | CBD 2 g/kg i.p. | |
|---|---|---|---|---|---|---|---|---|---|---|
| | Male | Female | Male | Female | Male | Female | Male | Female | Male | Female |
| Body weight (g) | 47±2.0 | 40±1.4 | 47±1.6 | 40±2.6 | 44±3.7 | 39±2.5 | 45±2.5 | 41±2.4 | 46±2.5 | 40±3.4 |
| Relative weight (%) | | | | | | | | | | |
| Liver | 5.1±0.15 | 4.2±0.13 | 4.7±0.18 | 4.2±0.19 | 4.9±0.19 | 4.6±0.14 | 4.3±0.20 | 4.5±0.14 | 4.5±0.14 | 4.5±0.20 |
| Kidneys | 1.5±0.02 | 1.0±0.01 | 1.3±0.02 | 1.0±0.01 | 1.4±0.01 | 1.0±0.03 | 1.3±0.01 | 1.0±0.02 | 1.3±0.01 | 1.0±0.01 |
| Spleen | 0.4±0.04 | 0.5±0.04 | 0.4±0.02 | 0.5±0.08 | 0.4±0.06 | 0.5±0.06 | 0.4±0.06 | 0.5±0.06 | 0.4±0.06 | 0.5±0.06 |
| Absolut weight (g) | | | | | | | | | | |
| Liver | 2.4±0.15 | 7.7±0.09 | 2.2±0.13 | 1.7±0.12 | 2.1±0.12 | 1.8±0.12 | 2.1±0.12 | 1.8±0.05 | 2.1±0.12 | 1.8±0.05 |
| Kidneys | 0.7±0.04 | 0.4±0.02 | 0.6±0.04 | 0.4±0.02 | 0.6±0.03 | 0.4±0.03 | 0.6±0.03 | 0.4±0.01 | 0.6±0.03 | 0.4±0.01 |
| Spleen | 0.2±0.02 | 0.2±0.01 | 0.2±0.01 | 0.2±0.03 | 0.2±0.03 | 0.2±0.03 | 0.2±0.03 | 0.2±0.02 | 0.2±0.03 | 0.2±0.02 |

Figure 4

| Treatment (µg/plate) | TA98 | | TA100 | |
|---|---|---|---|---|
| | $-S_9$ | $+S_9$ | $-S_9$ | $+S_9$ |
| C- | 20±2.1 | 22±3.6 | 154±8.6 | 229±14.1 |
| CBD 62.5 µg/plate | 18 ± 2.2 | 20 ± 4.2 | 150 ± 8.5 | 197 ± 7.8 |
| CBD 125 µg/plate | 19 ± 3.1 | 19 ± 5.4 | 149 ± 6.9 | 199 ± 7.5 |
| CBD 250 µg/plate | 18 ± 4.2 | 18 ± 5.1 | 149 ± 7.3 | 198 ± 6.5 |
| CBD 375 µg/plate | 17 ± 3.5 | 21 ± 6.3 | 148 ± 7.2 | 203 ± 5.5 |
| C+ | 1935 ± 208*** | 2124 ± 305*** | 1863 ± 121*** | 2332 ± 115*** |

Figure 7

| Treatment (µg/plate) | TA98 | | TA100 | |
|---|---|---|---|---|
| | $-S_9$ | $+S_9$ | $-S_9$ | $+S_9$ |
| CBD 62.5 µg/plate | 0.86 | 0.90 | 0.99 | 0.80 |
| CBD 125 µg/plate | 0.83 | 0.87 | 0.86 | 1.01 |
| CBD 250 µg/plate | 0.79 | 0.92 | 0.96 | 0.97 |
| CBD 375 µg/plate | 0.80 | 0.79 | 0.89 | 1.00 |

Figure 8

| Category | Symptoms | Placebo | CBD-SINT (17 mg/kg) | CBD-SINT (51 mg/kg) | CBD-SINT (170 mg/kg) |
|---|---|---|---|---|---|
| Excitation | Convulsions | (-) | (-) | (-) | (-) |
| | Tremors | (-) | (-) | (-) | (-) |
| | Increased activity | (-) | (-) | (-) | (-) |
| | Jumps | (-) | (-) | (-) | (-) |
| | Increased fear | (-) | (-) | (-) | (-) |
| | Increased touch reactivity | (-) | (-) | (-) | (-) |
| | Aggression | (-) | (-) | (-) | (-) |
| Stereotypes | Neck contractions | (-) | (-) | (-) | (-) |
| | Head movements | (-) | (-) | (-) | (-) |
| | Chewing | (-) | (-) | (-) | (-) |
| | Sniffing | (-) | (-) | (-) | (-) |
| | Scratching | (-) | (-) | (-) | (-) |
| Motor | Catalepsy | (-) | (-) | (-) | (-) |
| | Hypokinesia | (-) | (-) | (-) | (-) |
| | Gait abnormalities | (-) | (-) | (-) | (-) |
| | Motor incoordination | (-) | (-) | (-) | (-) |
| | Traction loss | (-) | (-) | (-) | (-) |
| | Snatch | (-) | (-) | (-) | (-) |
| Sedation | Decreased activity | (-) | (-) | (-) | (-) |
| | Decreased fear | (-) | (-) | (-) | (-) |
| | Decreased touch reactivity | (-) | (-) | (-) | (-) |
| Pain | Abdominal contortions | (-) | (-) | (-) | (-) |
| | Analgesia | (-) | (-) | (-) | (-) |
| Autonomic changes | Ptosis | (-) | (-) | (-) | (-) |
| | Exophthalmos | (-) | (-) | (-) | (-) |
| | Myosis | (-) | (-) | (-) | (-) |
| | Mydriasis | (-) | (-) | (-) | (-) |
| | Piloerection | (-) | (-) | (-) | (-) |
| | Defecation | (-) | (-) | (-) | (-) |
| | Diarrhea | (-) | (-) | (-) | (-) |
| | Salivation | (-) | (-) | (-) | (-) |
| | Tearing | (-) | (-) | (-) | (-) |
| Others | Increased breathing | (-) | (-) | (-) | (-) |
| | Decreased breathing | (-) | (-) | (-) | (-) |
| | Hypothermia | (-) | (-) | (-) | (-) |
| | Hyperthermia | (-) | (-) | (-) | (-) |

Figure 9

| Parameter | Placebo | CBD-SINT (17 mg/kg) | CBD-SINT (51 mg/kg) | CBD-SINT (170 mg/kg) |
| --- | --- | --- | --- | --- |
| Respiratory rate | 57 ± 6.01 | 55 ± 6.48 | 57 ± 5.43 | 56 ± 5.66 |
| Blood gases | | | | |
| pH | 7.25 ± 0.02 | 7.28 ± 0.04 | 7.25 ± 0.03 | 7.23 ± 0.04 |
| $PCO_2$ (mmHg) | 55.90 ± 1+70 | 56.85 ± 2.42 | 56.42 ± 2.21 | 56.52 ± 2.11 |
| $PO_2$ (mmHg) | 80.53 ± 3.13 | 71.83 ± 4.76 | 75.44 ± 4.51 | 76.34 ± 5.51 |
| $SO_2$ (%) | 82.65 ± 6.31 | 88.78 ± 1.75 | 86.71 ± 1.88 | 87.62 ± 1.91 |
| Hct (%) | 37.98 ± 2.71 | 38.25 ± 2.36 | 37.44 ± 2.51 | 38.51 ± 2.45 |
| tHb (g/dL) | 13.85 ± 0.88 | 13.45 ± 1.13 | 13.55 ± 1.11 | 13.35 ± 1.21 |
| Electrolytes | | | | |
| $Na^+$ (mmol/L) | 143.10 ± 0.82 | 144.40 ± 0.85 | 142.23 ± 0.79 | 143.21 ± 0.88 |
| $K^+$ (mmol/L) | 4.31 ± 0.12 | 4.35 ± 0.22 | 4.32 ± 0.18 | 4.34 ± 0.20 |
| $Ca^{++}$ (mmol/L) | 1.07 ± 0.02 | 1.04 ± 0.01 | 1.06 ± 0.02 | 1.04 ± 0.02 |
| $Cl^-$ (mmol/L) | 103.30 ± 0.68 | 104.50 ± 0.53 | 103.45 ± 0.61 | 103.35 ± 0.59 |
| Metabolites | | | | |
| Glycose (mg/dL) | 295.30 ± 18.93 | 303.80 ± 20.88 | 299.91 ± 21.31 | 300.01 ± 19.22 |
| Lactate (mmol/L) | 10.5 ± 0.11 | 1.22 ± 0.22 | 1.12 ± 0.21 | 1.15 ± 0.20 |
| Oximetry | | | | |
| $O_2Hb$ (%) | 88.75 ± 1.82 | 82.67 ± 3.59 | 85.13 ± 2.88 | 84.15 ± 3.02 |
| HHb (%) | 14.15 ± 1.22 | 11.50 ± 1.59 | 13.20 ± 1.33 | 13.02 ± 1.75 |
| Calculated values | | | | |
| P50 (mmHg) | 38.03 ± 2.02 | 40.35 ± 0.99 | 39.22 ± 1.18 | 40.25 ± 1.15 |
| $H^+$ (nmol/L) | 53.18 ± 5.17 | 52.58 ± 3.72 | 51.47 ± 2.99 | 52.21 ± 3.01 |
| BE (nmol/L) | -3.70 ± 0.47 | -3.47 ± 0.28 | -3.61 ± 0.33 | -3.55 ± 0.29 |
| $BE_{ecf}$ (nmol/L) | -3.07 ± 0.77 | -3.10 ± 0.14 | -3.13 ± 0.41 | -3.10 ± 0.52 |
| BB (mmol/L) | 43.80 ± 0.54 | 43.90 ± 0.63 | 43.65 ± 0.59 | 43.85 ± 0.61 |
| $cHCO_3$ (mmol/L) | 93.68 ± 0.61 | 90.50 ± 1.78 | 92.45 ± 0.99 | 91.35 ± 0.85 |
| $_{ct}CO_2$ (B) (mmol/L) | 23.63 ± 0.39 | 24.98 ± 0.92 | 23.44 ± 0.57 | 24.01 ± 0.51 |
| $_{ct}CO_2$ (P) (mmol/L) | 21.55 ± 0.73 | 22.95 ± 0.76 | 21.35 ± 0.71 | 22.06 ± 0.75 |
| $_{ct}O_2$ (vol%) | 15.83 ± 1.04 | 15.38 ± 0.59 | 15.54 ± 0.85 | 15.29 ± 0.77 |

Figure 10

PHARMACEUTICAL COMPOSITION, EXCIPIENT FOR THE COMPOSITION AND USE OF THE COMPOSITION

CROSS REFERENCE TO RELATED APPLICATIONS

This application is the US National Phase of and claims the benefit of and priority on International Application No. PCT/BR2019/050040 having a filing date of 11 Feb. 2019, which claims priority on and the benefit of Brazilian Patent Application No. 102018002843-0 having a filing date of 9 Feb. 2018.

FIELD OF THE INVENTION

The present invention discloses a composition and its use as a medicament for the treatment of neurological disorders to be administered preferably in humans and can also be used for treating animals. The present invention is in the field of Pharmacy and Medicine.

BACKGROUND OF THE INVENTION

Parkinson's disease is a chronic, progressive disease affecting one in every thousand people and directly affecting the patients' life quality. It is a pathology resulting from the death of dopamine-producing neurons from the substantia nigra, having an idiopathic etiology. It is believed its appearance comes from environmental and genetic factors, being able to interact and contribute to the development of neurodegeneration.

When signs and symptoms are detected, the loss of approximately 60% dopaminergic neurons has probably already occurred, and the dopamine content in the striatum is already about 80% lower than normal. Given this, the development of drugs and more in-depth research for the treatment of Parkinson's disease are relevant The main symptoms of this disease are slowness, stiffness, resistance to passive movement, difficulty in postural balance and tremor. In advanced stages, dementia, cognitive impairment, and extension of the brain morbid process can occur. The treatments available on the market treat the symptoms, but do not change the degenerative process. Over time, as the patient's clinical condition worsens, there is greater difficulty in controlling symptoms.

The main drugs currently indicated for Parkinson's disease are: triexiphenidyl hydrochloride, levodopa+benserazide hydrochloride, rasagiline mesylate, levodopa+carbidopa, among others.

Cannabidiol has shown to be a promising alternative for several neurological disorders, highly effective and devoid of psychotoxicity and other side effects. The neuroprotective action proposed in this invention, which slows down the progression of Parkinson's disease and other neurological diseases and minimizes the worsening of the patient's clinical condition, decreasing the extent of the morbid process related to the dopaminergic system to other brain areas, being unprecedented.

In the last 10 years there has been a notable increase in scientific publications on Cannabidiol, mainly stimulated by the discovery of its anti-inflammatory, antioxidative and neuroprotective effects. These studies have suggested a wide range of possible therapeutic effects of the asset in various therapeutic indications.

There are data from preclinical studies that used the striatal lesion model of rats with the 6-hydroxy dopamine toxin and the active decreased the degeneration of dopaminergic neurons and the activation of microglial cells. However, the mechanisms responsible for these effects are not elucidated.

Considering there are not enough pre-clinical studies to characterize the therapeutic potential of Cannabidiol in the treatment of Parkinson's disease, nor the pharmaceutical formulation for such indication, the present invention goes beyond these generic and preliminary teachings, describing and proving the feasibility of formulation of such indication.

Functional motor analysis and comorbidities usually accompanying Parkinson's disease need to be proven with synthetic Cannabidiol, Cannabidiol of plant origin and/or association.

In the search for the state of the art in scientific and patent literature, the following documents dealing with the subject matter were found:

The document WO 2009/020666, entitled "ORAL CANNABINOID LIQUID FORMULATIONS AND METHODS OF TREATMENT", discloses a liquid oral composition of cannabinoids, wherein the solvent is aqueous, and has a more efficient in vivo absorption profile than commercial gelatin capsules.

The document U.S. Pat. No. 7,025,992, entitled "Pharmaceutical formulations", discloses a formulation of powder cannabinoids, which when hydrated, has its absorption facilitated by means of an emulsifier.

The document WO 2015/068052, entitled "TERPENE AND CANNABINOID FORMULATIONS", discloses liposomes comprising cannabinoids and terpenes.

The document BR 10 2015 024165 8, entitled "ORAL PHARMACEUTICAL COMPOSITION UNDERSTANDING CANABINOID, PROCESS FOR ITS PREPARATION AND USE", discloses an oral pharmaceutical composition comprising cannabinoids, a process for its preparation and use.

Thus, what depends on the researched literature, no documents were found anticipating or suggesting the teachings of the present invention, so that the formulation proposed herein has novelty and inventive activity in view of the state of the art.

Briefly, there are noted several formulations for the treatment of neurological disorders.

SUMMARY OF THE INVENTION

Thus, the present invention describes two new formulations comprising cannabidiol (CBD) of synthetic and vegetal origin, respectively, and which has surprising neuroprotective activity, as well as for the treatment of several neurological disorders.

In a first object, the present invention discloses a pharmaceutical composition containing the active ingredient Cannabidiol of synthetic origin, and with: up to 0.06% cannabinol, up to 0.06% Delta-8-tetrahydrocannabinol, up to 0.06% Delta-9-tetrahydrocannabinol, up to 0.06% cannabidiolic acid methyl ester, up to 0.06% menthadienol and up to 0.06% methyl olivetolate.

In a second object, the present invention discloses an excipient for composition comprising oil of vegetable, animal or mineral origin or a combination thereof.

In a third object, the present invention discloses the use of the pharmaceutical composition with neuroprotective action.

In a fourth aspect, the present invention discloses the use of the pharmaceutical composition for the preparation of a medicament for the treatment of neurological disorders.

These and other objects of the invention will be immediately appreciated by those skilled in the art and will be described in detail below.

BRIEF DESCRIPTION OF THE DRAWINGS

The following figures are showed:

FIG. 1 shows a table with general appearance data and behavioral changes in rats (male and female) treated acutely with CBD-SINT during the first 8 hours after administration.

FIG. 2 shows a table with general appearance data and behavioral changes in mice (male and female) treated acutely with CBD-SINT during the first 8 hours after administration.

FIG. 3 shows a table with data on the effects of acute treatment with CBD-SINT on absolute (g) and relative (%) organ weight and final body weight of rats (male and female) after 14 days of exposure. Relative weight (%)=(absolute organ weight×100)/final body weight. Values are expressed as the mean±standard error of the mean (n=6). One-way ANOVA followed by Dunnett's test.

FIG. 4 shows a table with data on the effects of acute treatment with CBD-SINT on absolute (g) and relative (%) organ weight and final body weight of mice (male and female) after 14 days of exposure. Relative weight (%)= (absolute organ weight×100)/final body weight. Values are expressed as the mean±standard error of the mean (n=6). One-way ANOVA followed by Dunnett's test.

FIG. 7 shows a table with CBD-SINT mutagenicity data with (+S9) and without (−S9) metabolic activation for two strains of *Salmonella typhimurium* (TA98 and TA100). Values presented as mean±standard deviation. Negative control (C−)=bidistilled water; Positive control (C+)=TA98 (−S9) nitrophenylenediamine; TA98 (+S9) 2-anthramine; TA100 (−S9) sodium azide; TA100 (+S9) 2-anthramine. *** $p<0.001$ (one-way ANOVA followed by Dunnett's test).

FIG. 8 shows a table with CBD-SINT mutagenicity ratio (RM) data with (+S9) and without (−S9) metabolic activation for two strains of *Salmonella typhimurium* (TA98 and TA100).

FIG. 9 shows a table with data on the effects of acute treatment with CBD-SINT on the clinical behaviors and signs observed in the modified Irwin test. The evaluation time was 0-15 min, 15, 30, 60, 120, 180 min and 24 h after the acute administration of CBD-SINT or placebo. (−): Absence of the symptom.

FIG. 10 shows a table with data on the effects of acute treatment with CBD-SINT on respiratory rate, gases, electrolytes, and blood metabolites. PCO2: partial pressure of carbon dioxide; PO2: partial pressure of oxygen; SO2: hemoglobin saturation by oxygen; Htc: hematocrit; tHb: hemoglobin; Na+: sodium; K+: potassium; Ca++: calcium; Cl−: chloride; O2Hb: Ox Hemoglobin; HHb: Deoxyhemoglobin; P50: half of the maximum hemoglobin saturation; H+: dissociated hydrogen ion; BE: excess of base; BEecf: excess of base in the extracellular liquid compartment; BB: buffer base; cHCO3: bicarbonate concentration; ctCO2 (B): concentration of total carbon dioxide in whole blood; ctCO2 (P): concentration of total carbon dioxide in the plasma; ctO2: total oxygen concentration.

DETAILED DESCRIPTION OF THE INVENTION

Figure 5:
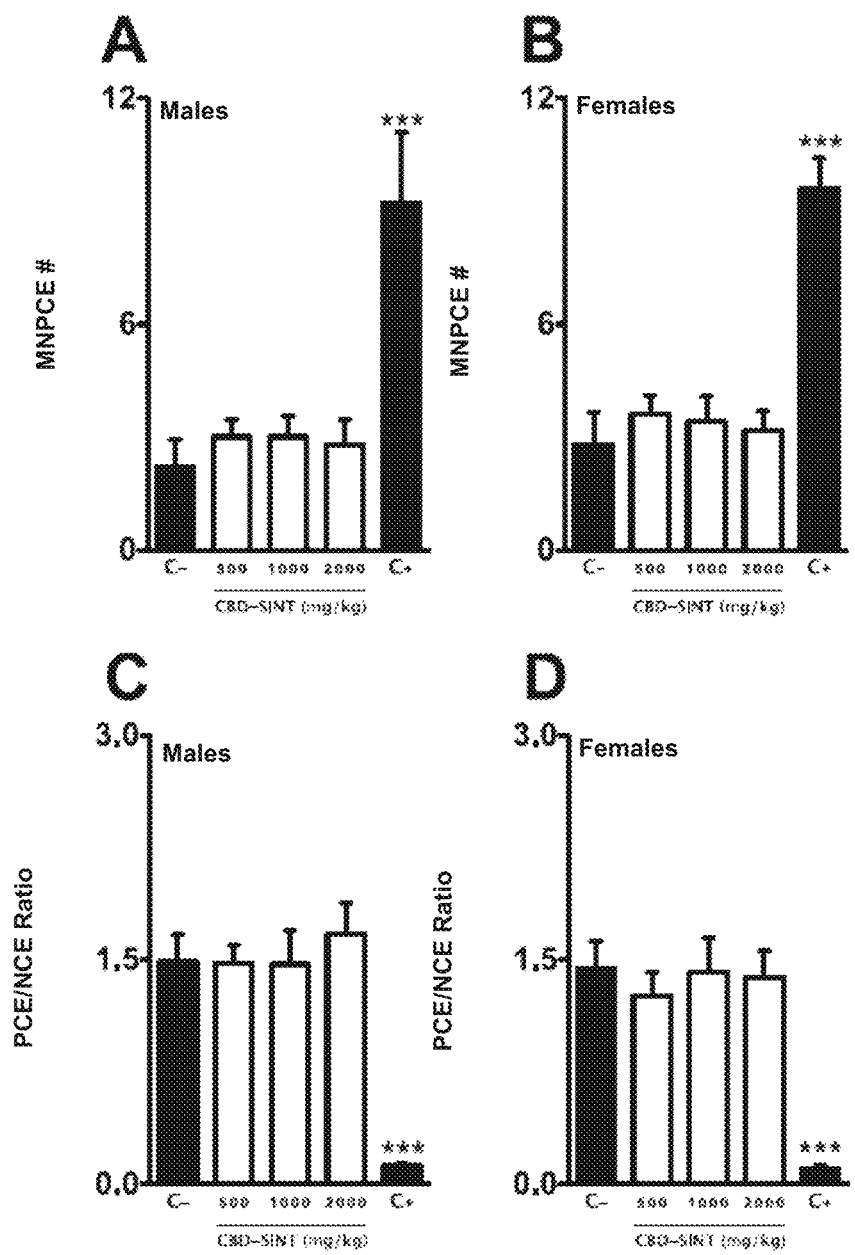
FIG. 5 shows the average number of micronucleated polychromatic erythrocytes (MNPCE) among the different experimental groups obtained during the micronucleus test.

The present invention discloses a pharmaceutical composition comprising from 50 to 400 mg active ingredient Cannabidiol of synthetic origin, with: up to 0.06% cannabinol, up to 0.06% Delta-8-tetrahydrocannabinol, up to 0.06% Delta-9-tetrahydrocannabinol, up to 0.06% cannabidiolic acid methyl ester, up to 0.06% menthadienol and up to 0.06% methyl olivetolate. The present invention also discloses the use of this composition in the preparation of a medication for treating neurological disorders due to its neuroprotective action, having its administration orally at a dose between the Cannabidiol range from 100 to 1750 mg/day.

The present invention discloses a composition to favor bioavailability and/or modulate its release to reduce the administration of the daily dose, favoring the patient's compliance to the treatment.

The present invention discloses a composition for improving organoleptic properties of the active ingredient(s).

The present invention discloses the oral administration of the composition in oral pharmaceutical forms of hard gelatin capsule, soft capsule, tablet, coated tablet, orodispersible tablet, effervescent tablet, lozenge, syrup, suspension and/or solution.

The present invention is indicated for the treatment of neurological disorders, such as refractory epilepsy, epilepsy, schizophrenia, sleep disorders, post-traumatic disorder, neuropathic pain, chronic pain relief and autism, preferably for therapeutic indication related to Parkinson's disease treatment, and is preferably indicated for the treatment of humans, and may be indicated for pathologies involving small, medium and large animals.

The present description aims to deepen the detail about the inventive concept, provide examples facilitating the cognition/understanding of it and provide precise technical data on some of the ways to embodiment the inventive concept of creation. The detailed description also aims to avoid the repetition, by third parties, of the extensive experimentation, financial investments, time, and intellectual activity that the inventors/applicants made to solve the technical problems herein solved.

Process of Obtaining Synthetic Cannabidiol

In a process of obtaining synthetic cannabidiol comprises the following steps:

a. Condensation reaction, starting with the compounds menthadienol and methyl olivetolate, to obtain the cannabidiolic acid methyl ester.
b. Decarboxylation saponification reactions, starting from the cannabidiolic acid methyl ester previously obtained, to obtain the crude synthetic Cannabidiol.
c. Filtration of the crude Cannabidiol obtained.
d. Crystallizing of crude Cannabidiol obtained.
e. Recrystallizing of crude Cannabidiol obtained.
f. Drying of the crude Cannabidiol obtained.

It is considered as the scope of the present invention the development of a composition comprising synthetic Cannabidiol, which is a synthetic cannabinoid and Cannabidiol phytopharmaceutical which is a cannabidiol of vegetal origin.

For the purposes of this invention, synthetic cannabinoids are compounds capable of interacting with cannabinoid receptors and which are found neither endogenously nor in plants.

Also, within the scope of the present invention are the pharmaceutically salts and acids of the above compound (s), as well as its mixture with other cannabinoids.

The therapeutic dose of oral administration from the formulation based on Cannabidiol ranges from 100 to 1750 mg/day, preferably between 300 and 850 mg/day in a single dose or divided throughout the day.

The oral compositions of the present invention has Cannabidiol concentration within the specifications set in the analytical methodology object of this patent, remaining stable for long periods of time, including the period of storage and expiration, with no considerable appearance of degradations such as Delta-9-tetrahydrocannabinol or other psychoactive compound.

The excipients used in the composition of the present invention are those excipients commonly found in the prior art and known to those skilled in the pharmaceutical field. Non-limiting examples include antioxidants, sweeteners, preservatives, opacifiers, lubricants, disintegrants, diluents and combinations thereof.

The antioxidant can be selected from acetylcysteine tocopherols, α-tocopherol, d-α-tocopherol, DL-α-tocopherol, ascorbyl palmitate, butylhydroxyanisol (BHA), butylhydroxytoluene (BHT), lecithin, cysteine, cysteine hydrochloride, propyl gallate, ascorbic acid, isoascorbic acid, thioglycerol, citric acid, tartaric acid, EDTA and its salts, hydroxyquinoline sulfate, phosphoric acid, sodium metabisulfite and sodium citrate, t-butylhydroquinone (TBHQ) and combinations of the same.

Sweetening agents can be selected from sucralose, saccharin, sodium saccharin, sodium cyclamate, sorbitol, xylitol, sucrose, glycerol, neohesperidine, aspartame and combinations thereof.

Preservatives can be selected from sodium benzoate, potassium sorbate, benzyl alcohol, paraben esters (hydroxybenzoic acids) such as methyl paraben, ethyl paraben, propyl paraben, butyl paraben and the like, and combinations thereof.

Disintegrants can be selected from crospovidone, croscarmellose, starch glycolate, polyacrylin potassium, hydroxypropyl cellulose, microcrystalline cellulose, or a combination thereof.

Lubricants can be selected from magnesium stearate, sodium stealyl fumarate, stearic acid, sodium citrate, or a combination thereof.

Diluents can be selected from various polyols (e.g. maltitol, mannitol and xylitol), microcrystalline cellulose, starch, talc, maltodextrin, sucrose and dextrose, oils of vegetal, animal, or mineral origin, or a combination thereof.

Oily solvents can be chosen from the group comprising grape seed oil, sesame oil, corn oil, soybean oil, olive oil, sunflower oil, canola oil, walnut oil, linseed oil, avocado oil, mint oil, peanut oil, hydrogenated castor oil, coconut oil, açai oil, andiroba oil, babassu oil, buriti oil, Brazil nut oil, copaiba oil, passion fruit, pracaxi oil, pataua oil, triglycerides, primrose oil, safflower oil, almond oil, borage oil, pomegranate seed oil, sea buckthorn oil, garlic oil, krill oil, liver oil cod, palm oil, fish oil, hydrogenated castor oil, macadamia oil, rosehip oil, cotton oil, and combinations thereof.

Preferably, the oily solvent is corn oil.

Preparation Process of Pharmaceutical Composition

Production process uses usual equipment for the preparation of solid pharmaceutical forms, such as: vibrating screens, pharmaceutical mixers ("V" mixer, Double-Cone mixer, BIN mixer and/or High shear mixer), bed fluidized, stove, roller-compactor, rotary-type pharmaceutical presses and encapsulators, coating machines (drilled pan and dredgers), agitators and colloidal/ultra turrax mill.

Production process uses usual equipment for the preparation of pellets, such as: vibrating screens, casters, preparation tanks, pharmaceutical mixers, top and bottom spray fluidized beds, extruders, spheronizers and encapsulators.

Production process uses usual equipment for the preparation of soft capsules, such as: vibrating screens, pharmaceutical mixers, reactors, agitator tanks, colloid mill, encapsulators, drying tunnels, greenhouses, and air-conditioned chambers. This production process basically consists of 4 steps: 1. Preparation of the melted gelatin mass; 2. Preparation of filling with the active; 3. Encapsulation; and 4. Drying the capsules. The required material amounts at each stage are proportional to the number of capsules to be prepared.

A process for preparing a composition of the present invention comprises the steps of:

a. Dissolution of the active(s) in solvent or co-solvent, followed by addition of the other adjuvants and homogenization, with or without heating, and/or
b. Dissolution of the active(s) in solvent or co-solvent, followed by the addition of other adjuvants and homogenization and incorporation into support for transdermal administration, and/or
c. Dissolution or suspension of the active(s) in solvent or co-solvent, followed by addition of other adjuvants and homogenization and incorporation into support for nasal and/or pulmonary administration, and/or d. Addition of active(s) and excipients, homogenization, and encapsulation, and/or e. Addition of active(s) and excipients, micro-spherization, homogenization and encapsulation.

f. Addition of active(s) and excipients, micro-spherization, homogenization and compression, and/or g. Addition of active(s) and excipients, homogenization, compression, and coating, and/or h. Addition of active(s) and excipients, homogenization, granulation, and compression.

i. Incorporation of the active in liposomal systems, nanoparticles and/or nano-capsules.

It is a further object of the present invention the preparation process employing nanotechnology, liposomes, pellets, microemulsions and adhesives.

The proposed formulations should have adequate reproducibility, through a large-scale production process duly validated.

In a first object, the present invention has a pharmaceutical composition containing the active ingredient Cannabidiol from synthetic origin, and with: up to 0.06% cannabinol, up to 0.06% Delta-8-tetrahydrocannabinol, up to 0.06% Delta-9-tetrahydrocannabinol, up to 0.06% cannabidiolic acid methyl ester, up to 0.06% menthadienol and up to 0.06% methyl olivetolate.

In one embodiment of the composition, it has a range of Cannabidiol of synthetic origin between 50 to 400 mg.

In one embodiment of the composition, it has oral dosage forms of hard gelatin capsule, tablet, coated tablet, orodispersible tablet, effervescent tablet, lozenge, syrup, suspension and/or solution, in particular soft gelatin capsule.

In a second object, the present invention has excipients for composition comprising oil of vegetal, animal, or mineral origin, or a combination thereof.

In one embodiment of the excipient, the oil can be selected from the group comprising grape seed oil, sesame oil, corn oil, soybean oil, olive oil, sunflower oil, canola oil, walnut, linseed oil, avocado oil, mint oil, peanut oil, hydrogenated castor oil, coconut oil, acai oil, andiroba oil, babassu oil, buriti oil, Brazil nut oil, oil of copaiba, passion fruit oil, pracaxi oil, pataua oil, triglycerides, primrose oil, safflower oil, almond oil, borage oil, pomegranate seed oil, sea buckthorn oil, garlic oil, garlic oil krill, cod liver oil, palm oil, fish oil, hydrogenated castor oil, macadamia oil, rosehip oil, cotton oil, or combinations thereof.

In an embodiment of the excipient, the selected oil is corn oil.

In a third object, the present invention has the use of the pharmaceutical composition with neuroprotective action.

In one embodiment of the neuroprotective action, it is administered at a dose between 100 to 1750 mg/day.

In a fourth object, the present invention has the use of the pharmaceutical composition for the preparation of a medication for treating neurological disorders.

In one embodiment of neurological disorders, they can be refractory epilepsy, epilepsy, schizophrenia, sleep disorders, post-traumatic disorder, Alzheimer's disease, anxiety, depression, bipolar disorder, neuropathic pain, chronic pain relief, autism, chronic pain relief, and Parkinson's disease.

In one embodiment of the neurological disorder, it is preferably Parkinson's disease.

In an embodiment of the Cannabidiol dose, it is in the range between 300 to 850 mg/day, preferably.

In one embodiment of the Cannabidiol dose, it can be a single dose or divided throughout the day.

In the present invention, it is understood by:

Neuroprotective activity: as used herein, the term "neuroprotective" activity refers to neuroprotection, that is, mechanisms and strategies used to protect neurons against damage resulting from diseases affecting the Central Nervous System.

Neurological disorders: as used herein, the term "neurological disorders" refers to diseases affecting the brain, spine and its respective nerves that connect them. Some examples include: refractory epilepsy, epilepsy, schizophrenia, sleep disorders, post-traumatic disorder, Alzheimer's disease, anxiety, depression, bipolar disorder, neuropathic pain, chronic pain relief, autism, and Parkinson's disease.

Single dose (acute) toxicity study: as used herein, the term "single dose (acute) toxicity study" refers to a test to assess the short-term administration safety of a given compound on an animal.

Genotoxicity study: as used herein, the term "genotoxicity study" refers to a study of the action of any physical, chemical, or biological agent producing toxic and genotoxic effects on the genetic material.

Micronucleus test: as used herein, the term "micronucleus test" refers to a cytogenetic test for biomonitoring genotoxic damage.

Comet assay: as used herein, the term "comet assay" refers to a cytogenetic test for biomonitoring genotoxic damage.

AMES test: as used herein, the term "AMES test" refers to a short-term mutagenesis assay aimed at identifying substances with the potential to induce genetic mutations.

Open field test: as used herein, the term "open field test" refers to a test for the evaluation of motor activity of a given animal.

Morris water labyrinth (cued test): as used herein, the term "Morris water labyrinth (cued test)" refers to a test aimed at assessing the hippocampus related to learning and memory.

EXAMPLES

The examples shown herein are intended only to exemplify one of the countless ways of carrying out the invention, however without limiting the scope of it.

Example 1. Single Dose (Acute) Toxicity Study in Rats and Mice

The single-dose (acute) toxicity study was carried out with different groups of rats and mice (male and female) and according to the procedures recommended by OECD (2001) and ANVISA (2013).

After a 6 h-fasting period, the animals' body weight was determined, and the dose of the synthetic CBD was calculated. Two single doses (1000 and 2000 mg/kg) of synthetic CBD were administered orally (with the aid of a gavage probe) and intraperitoneally in different groups of rats and mice (male and female). Other different groups of rodents were treated with placebo and were considered as control groups.

The animals were carefully observed for any toxicity signs within the first eight hours after treatment, and daily for a period of 14 days. On the 15th day all animals were euthanized, and the respective anatomopathological investigations were performed on the 15th day after the treatments.

The acute administration effects of CBD-SINT in rats and mice on overall appearance and behavioral changes are shown in FIGS. 1 and 2.

During the first 8 hours of observation, animals treated with CBD-SINT at doses of 1000 mg/kg and 2000 mg/kg intraperitoneally showed a significant decrease in its activity. In addition, occasional abdominal contortions were also observed. After this period (8 h), all animals were active and with normal behavior. There were no significant changes in appearance or in the general behavior pattern until the end of the 14-days observation. The LD50 of CBD-SINT was not set forth because no deaths were observed in animals treated with doses up to 2000 mg/kg orally or intraperitoneally.

The final body weight of male and female rats and mice treated by oral and intraperitoneal routes, with different doses of CBD, are shown in FIGS. 3 and 4, respectively.

Final body weight and body weight gains over the entire treatment period were similar between the groups receiving the placebo or CBD-SINT. In addition, there was no change in daily feed and water consumption compared to placebo.

There were no significant differences in the absolute (g) or relative (%) weight of all organs isolated from rats and mice treated with CBD or placebo after 14 days of treatment (FIGS. 3 and 4).

Macroscopic examination of vital organs did not disclose any abnormalities among all experimental groups. No signs of inflammation, hemorrhage, fluid accumulation or other changes suggestive of lesions were observed in all tissues studied. In the histopathological analyzes, no significant changes were identified, suggesting the absence of acute toxicity for CBD-SI NT at the doses used.

Example 2. Genotoxicity Study in Rats

The doses of CBD used were determined from the Guide for Conducting Non-Clinical Toxicology and Pharmacological Safety Studies needed for Drug Development (ANVISA, 2013; Version 1.2)—short-term protocols. The following tests were performed:

Micronucleus Test

To perform the micronucleus test (Schmid, 1976), different groups of rats (male and female; n=10) received three doses of CBD (500, 1000 and 2000 mg/kg) orally. The negative control group received placebo by gavage and the positive control was treated with cyclophosphamide monohydrate (20 mg/kg—Sigma-Aldrich) intraperitoneally. After 24 hours (cyclophosphamide) and 48 hours (CBD-SINT and vehicle) the end of treatments, the animals were euthanized by decapitation. The femurs were removed, the proximal epiphysis was removed to expose the medullary canal and, with the aid of a 13×4.5 mm needle and 3 mL NaCl solution (150 mM), the marrow was removed, washing the medullary canal with NaCl solution. The material was transferred to glass tubes and centrifuged at 1000 rpm/5 min. After centrifugation, the supernatant was discarded, and the deposit was resuspended with a 4% formaldehyde solution and slightly homogenized with the aid of a Pasteur pipette. A drop of this cell suspension was placed on a clean, dry slide, and then the smear was performed. The slides were dried at room temperature and, after 24 hours, stained with Leishman eosin-methylene blue and subjected to microscopic analysis. To determine the number of micronuclei, 2000 polychromatic erythrocytes were counted per animal (1000 in each slide) using an optical microscope, at 400× magnification. The analysis of the slides was blind and performed by a single evaluator.

Comet Assay

To perform the comet assay, different groups of rats (male and female; n=10) received three doses of CBD-SINT (500, 1000 and 2000 mmg/kg) orally. The negative control group received placebo by gavage and the positive control was treated with cyclophosphamide monohydrate (20 mg/kg—Sigma-Aldrich) intraperitoneally. After 24 hours (cyclophosphamide) and 48 hours (CBD-SINT and vehicle) the end of the treatments, samples of peripheral blood were collected before the animals were euthanized. The obtaining of slides with cells run on electrophoresis gel for the assessment of DNA damage was performed according to the technique described by Klaude et al. (1996). A total of 10 µL cell suspension obtained by mixing with 120 µL of 5% LMP agarose at 37° C. was deposited on a slide pre-covered with normal agarose (1.5%) and taken to refrigeration at 4° C. for 10 min (covered with coverslips) for agarose hardening. After adding the cells to the slide, exposure to direct light (irradiation) was avoided to prevent further DNA damage. The coverslips were carefully removed, and the slides stored in the lysis solution in a refrigerator (4° C.) for 1 hour. After the lysis time, the slides were removed and placed in the horizontal electrophoresis vat, the alkaline electrophoresis buffer was added to cover it, then the vat was immersed in a container with ice (4° C.) for 25 minutes for DNA denaturation. Then, the electrophoresis run started with 25 volts and 300 milliamps. The running time was approximately 25 minutes. After electrophoresis, the slides were removed and neutralized with 5 mL buffer solution for 5 minutes, this procedure was repeated twice. After drying the slides, they were fixed with ethanol for 5 minutes and stored in the refrigerator until analysis. For analysis, the slides were stained with 100 µL of ethidium bromide, covered with coverslips, and analyzed after approximately 5 minutes. To visualize DNA damage, the slides were observed in 400× magnification using a fluorescence microscope equipped with a 515-560 nm excitation filter and a 590 nm barrier filter. 100 cells from each animal were analyzed.

AMES Test

For the AMES test, the TA 100 and TA 98 strains of *Salmonella typhimurium* were used. The strain TA 100, which detects mutagens causing base pair replacement in DNA, contains a mutation in the hisG gene (hisG46), which codes for the first histidine biosynthesis enzyme, with the CG pair as the preferred point for reversion. The strain TA 98 has a mutation in the hisD gene to reverse eight repetitive GC residues and detects mutagenic compounds causing the DNA reading frame to shift. According to the methodology of direct incorporation in plates, developed by Maron and Ames (1983), different concentrations of CBD-SINT (375, 250, 125 and 62.5 µg/plate) were mixed with 0.1 mL of the bacteria culture and 2 mL of surface agar (top agar), supplemented with traces of histidine and biotin. For the tests with metabolic activation, 0.5 mL homogenized microsomal fraction S9 of rat liver (post-mitochondrial fraction, supplemented with a cofactor, prepared from the liver of rodents treated with an enzymatic inducing agent, arochloror 1254) (MOLTOX—Molecular Toxicology, USA) were added. As a negative control, double-distilled water (vehicle) was used. As a positive control for TA98, 4-nirophenylenediamine (NPD) dissolved in DMSO was used at a concentration of 10 µg/plate. For the strain TA100, sodium azide, dissolved in double distilled water at a concentration of 1.25 µg/plate was used in tests with no metabolic activation. In the assays with metabolic activation, 2-anthramine (2-ANTR) was used as a mutagen at a concentration of 3 µg/plate for TA100 and TA98. The contents of each tube were slightly homogenized and poured over the surface of a plate containing minimal glycosylated agar. After solidification of the top agar, the plates were incubated for 48 hours at 37° C. After this period, the number of reversing colonies per plate was counted. The assay was performed in triplicate.

Regarding the micronucleus test, all animals (males and females) receiving CBD-SINT (500, 1000 and 2000 mg/kg) had the MNPCE number in a similar way to that found for animals treated only with placebo (C−). On the other hand, animals treated with cyclophosphamide (C+) showed a significant increase in the average number of MNPCE, showing the mutagenic potential of this substance.

Similar to the aforementioned data, the ratio of polychromatic/normochromatic erythrocytes (PCE/NCE ratio) was significantly changed by treatment with cyclophosphamide in all experimental groups (males and females). Thus, treatment with CBD-SINT did not cause any significant change in this parameter when compared to animals treated with placebo alone (FIG. 5).

Figure 6:
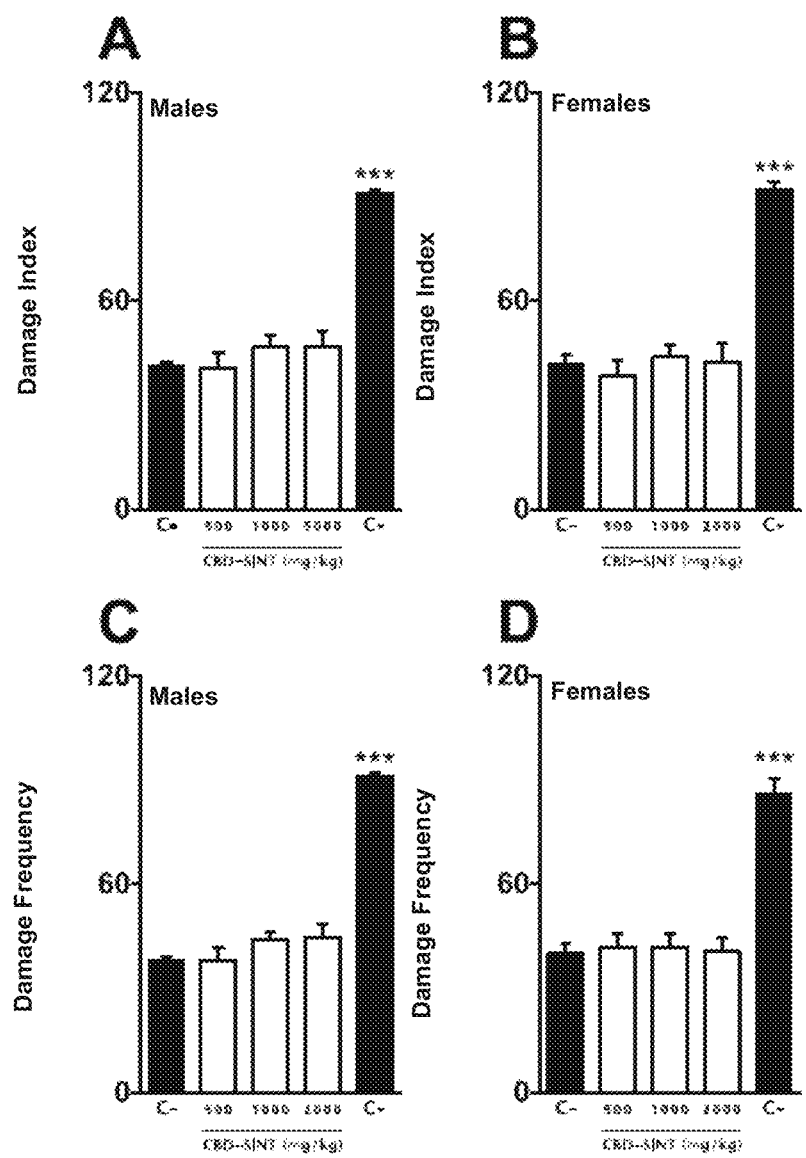
FIG. 6 shows the effects of acute treatment with CBD-SINT and cyclophosphamide on Damage Index (A and B) and Damage Frequency (C and D) to the DNA of male and female rats.

Regarding the comet assay, none of the tested doses of CBD-SINT induced any significant changes when compared to animals treated with the negative control (placebo). On the other hand, cyclophosphamide was able to induce an increase of approximately 100% in the index and frequency of damage in all groups tested (FIG. 6).

Regarding the AMES test, FIG. 7 shows the results obtained, indicating the mean and standard deviation of the number of his+/plate reversals, for the control groups (C+ and C−) and CBD, in the different concentrations tested, with strains of *Salmonella typhimurium* TA98 and TA 100 in the presence and absence of metabolic activation.

FIG. 8 shows the mutagenicity ratios (MR). It appears that there was no increase in the frequency of reversible mutants with the increase in CBD-SINT concentration and the mutagenicity ratios were all less than 2, indicating the absence of mutagenic activity.

Example 3. Pharmacological Safety Tests on the Central Nervous, Respiratory, and Cardiovascular Systems Male New Zealand rabbits (n=6 per group) were used for pharmacological safety tests. All tests were performed orally (route recommended for humans) and the investigated parameters were determined after a single administration of CBD-SINT. CBD-SINT doses were determined by allometric extrapolation from the average dose used in human patients (25 mg/kg).

The dose of 51 mg/kg was used as the intermediate dose, stipulating a higher and a lower dose. Three dose ranges were used according to the Guide for Conducting Non-Clinical Toxicology and Pharmacological Safety Studies Necessary for Drug Development (ANVISA, 2013; Version 1.2). Thus, the doses used were 17, 51 and 170 mg/kg of CBD-SINT.

The effects on three systems were evaluated:
Effects on Central Nervous System

Effects on the central nervous system were assessed in male rabbits according to the modified Irwin test (Roux et al., 2005).

After 6 h-fasting, three doses of CBD (17, 51 and 170 mg/kg) were administered to different groups of male rabbits by gavage. Placebo was administered to the control group (1 mL/kg). The solid diet was released to the animals 1 hour after the treatments.

The clinical and behavioral effects were assessed at 0-15 min, 15, 30, 60, 120 and 180 min and 24 h after administrations.

In order to observe possible behavioral and physiological changes, the following parameters were recorded: seizures, tremors, locomotor activity, jumping, fear-related behavior, reactivity to touch, aggression, neck contractions, stereotypes (head movements, chewing, sniffing, scratching), catalepsy, akinesia, gait, motor coordination, traction, abdominal contortions, analgesia, ptosis, exophthalmos, miosis, mydriasis, piloerection, defecation, diarrhea, salivation, tearing, breathing and body temperature.
Effects on Respiratory System After 6-h fasting, three doses of CBD-SINT (17, 51 and 170 mg/kg) were administered to different groups of male rabbits by gavage. Placebo was administered to the control group (1 mL/kg). One hour after treatments, all rabbits remained conscious in the prone position. The respiratory rate was determined using a Kofranyi-Michaelis respirometer (Murphy, 2002). For arterial blood gas analysis, arterial blood samples were taken from the central ear artery and immediately processed. All parameters below were determined on a Cobas b 221 multiparametric blood gas analyzer (Roche Diagnostics, Rotkreuz, Switzerland): pH, $PCO_2$ (mm Hg), $PO_2$ (mm Hg), $SO_2$(%), Htc (%), tHb (g/dL), Na+ (mmol/L), K+ (mmol/L), Ca2+ (mmol/L), Cl− (mmol/L), glucose (mg/dL), lactate (mmol/L), O2Hb (%), HHb (%), P50 (mm Hg), H+ (nmol/L), BE (nmol/L), BEecf (nmol/L), BB (mmol/L), $cHCO_3$ (mmol/L), $ctCO_2$ (B) (mmol/L), $ctCO_2$ (P) (mmol/L) and $ctO_2$ (% by volume).
Effects on Cardiovascular System The effects on cardiovascular system were evaluates by two tests:

a) Electrocardiography, wherein after a 6-h fasting, three doses of CBD (17, 51 and 170 mg/kg) were administered to different groups of male rabbits by gavage. Placebo was administered to the control group (1 mL/kg). One hour after treatments, all rabbits remained conscious in the supine position. Four electrodes (RL, RA, LL, and LA) were placed in the folds of both elbows and both knees. The V1 electrode was positioned in the 4th intercostal space to the right of the sternum. The V2 electrode was placed in the 4th intercostal space to the left of the sternum. The V3 electrode was positioned halfway between the V2 and V4 electrodes. The V4 electrode was positioned in the 5th intercostal space in the hemiclavicular line. The V5 electrode was positioned inside the axillary line at the same level as the V4 electrode. The V6 electrode was positioned on the middle axillary line at the same level as the V4 and V5 electrodes. A small amount of 70% gel alcohol was applied to each electrode interface for less interference and better electrical conduction. An acclimatization time of 5 min was waited, and then the cardiographic electric waves were recorded for 5 min. The electrocardiography was recorded with an ECG recorder (WinCardio, Micromed, Brasilia, Brazil).

b) Blood pressure measurement, after a 6-h fasting, three doses of CBD-SINT (17, 51 and 170 mg/kg) were administered to different groups of male rabbits by gavage. Placebo was administered to the control group (1 mL/kg). 40 minutes after treatments all rabbits were anesthetized with 10 mg/kg diazepam intramuscularly combined with 115 mg/kg ketamine. Then, the animals received a bolus injection of heparin (50 IU) subcutaneously. Tracheostomy was performed to allow animals to breathe spontaneously. Then, the left carotid artery was isolated, cannulated, and connected to a pressure transducer coupled to a PowerLab recording system (Chart 5.0, ADI Instruments, Castle Hill, Australia). After 15 minutes for hemodynamic stabilization, systolic blood pressure (SBP), diastolic blood pressure (DBP) and mean arterial pressure (MAP) were recorded for another 20 min.

Regarding the effects on the central nervous system, the results obtained in male rabbits are shown in FIG. 9.

During the entire observation period (24 h) none of the experimental animals was inactive or refused to consume food or water. In addition, no significant changes in the animals' behavior or physiological status were observed until the end of the 24 h.

Regarding the effects on respiratory rate and analysis of arterial blood gases, the results obtained are shown in FIG. 10.

The average respiratory rate of rabbits treated with placebo alone was 57±6.01 bpm. No increase or decrease in respiratory rate was observed after acute administration of CBD-SINT (17 mg/kg: 55±6.48; 51 mg/kg: 57±5.43; 170 mg/kg: 56±5.66). The analysis of arterial blood gases disclosed none of the CBD-SINT doses changed the pH, PCO2 (mm Hg), PO2 (mm Hg), SO2(%), Htc (%), tHb (g/dL), Na+ (mmol/L), K+ (mmol/L), Ca2+ (mmol/L), Cl- (mmol/L), glucose (mg/dL), lactate (mmol/L), O2Hb (%), HHb (%), P50 (mm Hg), H+ (nmol/L), BE (nmol/L), BEecf (nmol/L), BB (mmol/L), cHCO3 (mmol/L), ctCO2 (B) (mmol/L), ctCO2 (P) (mmol/L) or ctO2 (% by volume) when compared to animals treated with placebo alone.

Figure 11:
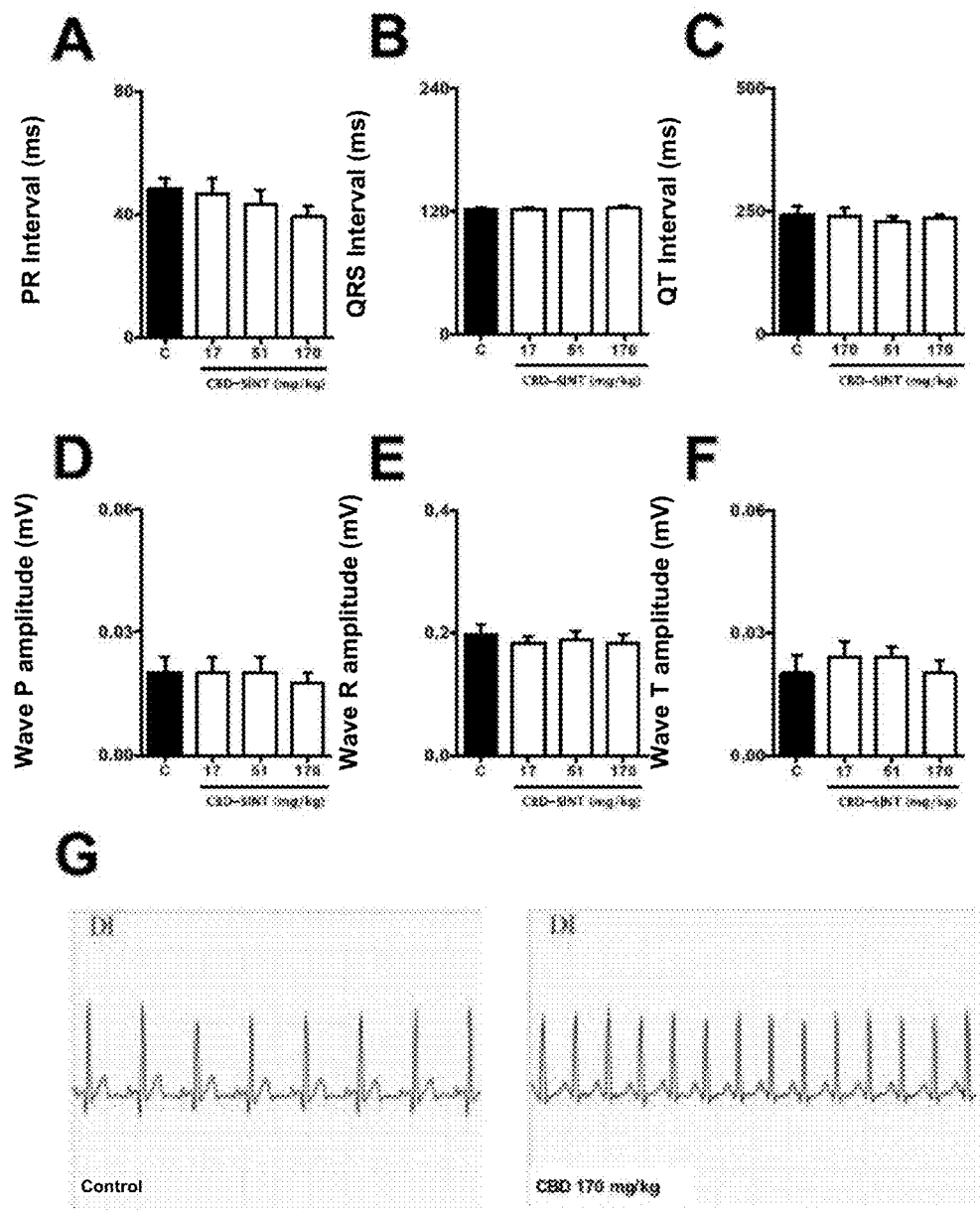
FIG. 11 shows representative electrocardiograms and quantitative data for rabbits treated with placebo or CBD-SINT at doses of 17, 51 and 170 mg/kg.

Regarding the effects on electrocardiography, no significant changes were observed in the PR, QRS or QT segments between the different experimental groups. In addition, no changes were found in the amplitudes of P, R or T waves when compared to animals treated with placebo alone (FIG. 11).

Figure 12:
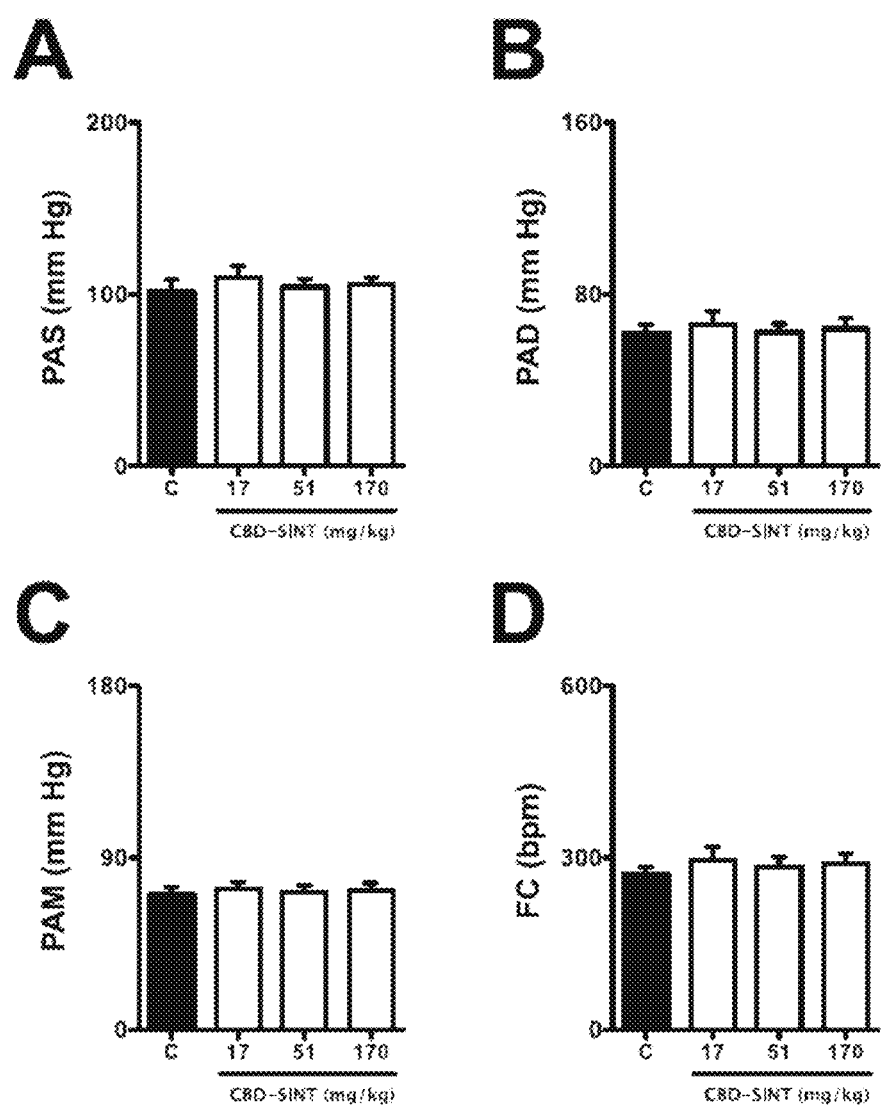
FIG. 12 shows the results obtained from systolic, diastolic, and mean arterial pressures recorded in animals from the control group.

Regarding the effects on blood pressure, the systolic, diastolic and mean arterial pressures recorded in animals in the control group (treated with placebo) after the stabilization period (15 minutes) were 101±6.7 mm Hg, 61±3.9 mm Hg and 72±3.9 mm Hg, respectively (FIG. 12).

Oral administration of CBD-SINT (17, 51 or 170 mg/kg) did not significantly change blood pressure levels compared to the control group (FIG. 12A-C). Similarly, heart rate was not significantly different between experimental groups. The mean values in the negative control (placebo) and CBD-SINT groups (17, 51 and 170 mg/kg) were 270±15 bpm, 285±18 bpm, 279±20 bpm, and 275±17 bpm, respectively (FIG. 12D).

Example 4. Neuroprotection Studies Against Behavioral Changes Induced by the Administration of 1-Methyl-4-Phenyl-1,2,3,6-Tetrahropyridine and 6-OHDA The number of animals per group was ten (10) subjects. This number was estimated based on internationally recognized and scientifically validated protocols. The doses of the CBD-SINT formulation were determined by allometric extrapolation from the average dose used in human patients (600 mg/day, which in a 70 kg individual represents approximately 9 mg/kg), obtaining an average dose of ~36 mg/kg CBD in rats.

For the calculation of the three doses, the intermediate dose was used as a reference, and then a higher and a lower dose was stipulated on a logarithmic scale. To stipulate the lowest dose, ⅓ of the median dose was used. For the higher dose, a safety factor of 10 times the lower dose was used. Thus, the doses of CBD-SINT used in this trial were: 12, 36 and 120 mg/kg.

Figure 13:
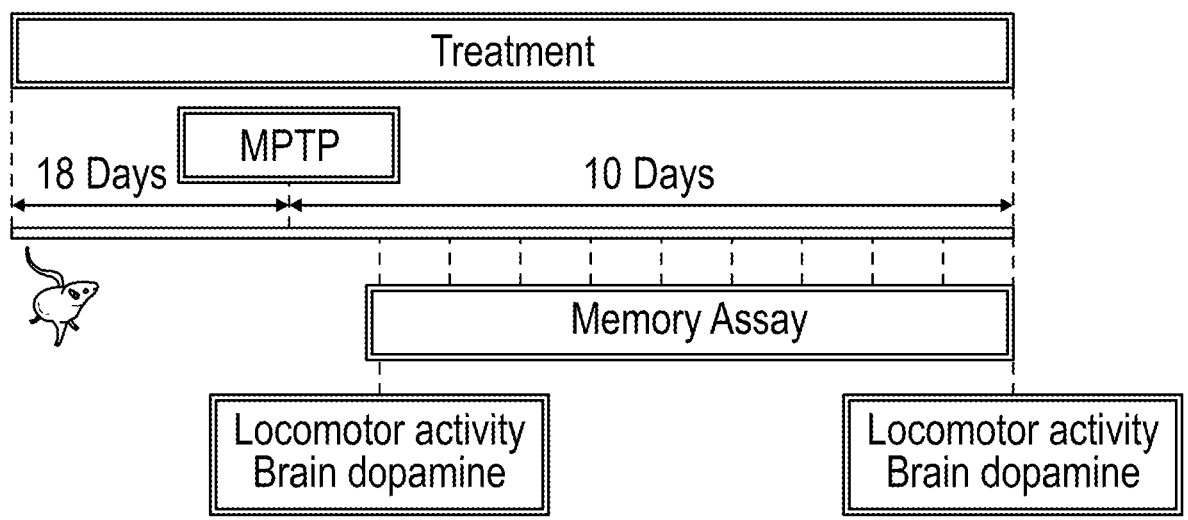
FIG. 13 shows the scheme used in the memory tests (Morris water maze) that were performed daily from day 1 to day 10 after the administration of the neurotoxin MPTP.

For the experiments with MPTP (neuroprotection), the animals were divided into the following experimental groups:
MPTP+placebo
MPTP+CBD-SINT 12 mg/kg
MPTP+CBD-SINT 36 mg/kg
MPTP+CBD-SINT 120 mg/kg
Sham+placebo
Naive CBD-SINT and placebo were administered orally (gavage) for 18 days prior to the administration of the neurotoxin by stereotactic surgery, and for another 10 days after surgery. After the administration of the neurotoxin, the behavioral (locomotor activity) and biochemical (brain dopamine dosage) parameters were evaluated after 24 hours and after 10 days. The memory tests (Morris water maze) were performed daily from day 1 to day 10 after the administration of the neurotoxin (FIG. 13).

For the experiments with 6-OHDA, the animals were divided into the following groups:
6-OHDA+placebo
6-OHDA+CBD-SINT 12 mg/kg
6-OHDA+CBD-SINT 36 mg/kg
6-OHDA+CBD-SINT 120 mg/kg
Sham+placebo
Naive After stereotaxic surgery for the administration of 6-OHDA, the rats had a recovery period of seven days until the start of treatments.

Figure 14:
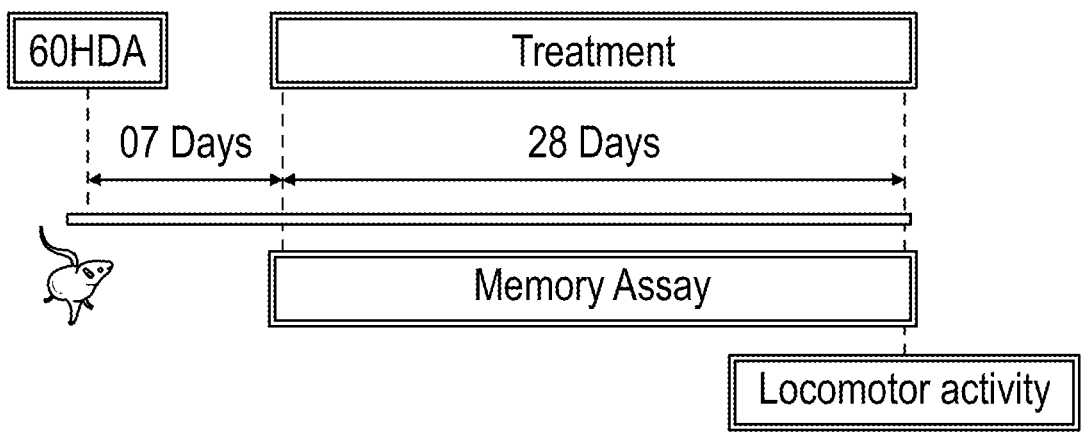
FIG. 14 shows the scheme used in the memory tests (Morris water maze) which were performed daily from day 18 to day 28 after the administration of neurotoxin 6-OHDA.

After the recovery period, CBD-SINT and placebo were administered orally (gavage) for 28 days. Locomotor activity tests were performed only at the end of treatments (day 28). The memory tests (Morris water maze) were performed daily from day 18 to day 28 (FIG. 14).

The animals subjected to stereotactic surgery were initially anesthetized with an association of ketamine (100 mg/kg) and xylazine (10 mg/kg) administered intraperitoneally. After anesthesia, 0.10 mL of G-procaine penicillin (20,000 U/0.05 mL-i.m.), atropine sulfate (0.4 mg/kg-i.p.) and lidocaine (0.2 mL with 2% vasoconstrictor-s.c.) in the dermis covering the animals' skull.

The rats were submitted to stereotactic surgery (stereotactic—David Kopf, model 957L) and received bilateral microinfusion of MPTP or 6-OHDA (different groups of rats) directly into the substantia nigra. For surgery, the following stereotaxic coordinates were used: anteroposterior: 5.0 mm from the bregma; mediolateral: ±2.1 mm from the midline and dorsoventral: −7.7 mm from the cranial vault (Paxinos and Watson, 1986). Then, 100 μg MPTP (diluted in 1 μL saline, with a flow of 0.33 μL/min) or 8 μg 6-OHDA (diluted in 2 μL saline with 0.2 μg/μL ascorbic acid, with a flow rate of 0.33 μL/min) were injected. The microinfusions were performed with the aid of a needle (30 gauge) connected to a polyethylene tube adapted to a 10 mL micro-syringe (Hamilton, USA), which in turn, is fitted into an infusion pump (Harvard Apparatus, USA). After the end of the microinfusion, the needle was kept in place for another 2 minutes to prevent reflux of the neurotoxins. Then, the scalp was sutured, and the animals were removed from the stereotaxic. The rats were then placed in its original cages. The animals in the Sham groups were subject to the same surgical procedure, however without receiving the neurotoxins, being only introduced to the needle in the same stereotactic coordinates. The rats of naive groups were not subject to stereotactic surgery but were removed from the housing cage for handling for a few hours.

To performing behavioral observations, the animals were subjected to three tests:

a) Open Field Test (Motor Activity)

Figure 15:
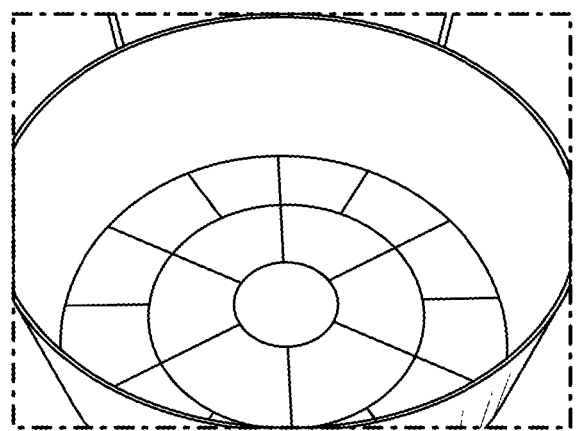
FIG. 15 shows the model used in the open field test.

The animals were placed on the central circle of the open field and its behavior evaluated for 5 minutes. This assessment included the frequency of locomotion (entering a room with all four legs), standing up (support only on the hind legs, with the trunk perpendicular to the arena floor), duration of immobility (without motor activity, completely paralyzed) and time of latency (time it takes for the animal to start moving after being placed in the center circle of the arena). Each animal was assessed individually, and the device was cleaned between animals with 5% alcohol solution (FIG. 15).

b) Morris Water Maze (Cued Test/Memory Version)

All experimental groups were tested in the Morris water maze.

The labyrinth consists of a black circular tank, 170 cm in diameter and 50 cm high, filled with water at a depth of 32 cm. The water and room temperatures are controlled and around 22±2° C. Initially four positions were established serving as a starting point for the rats, which are: north, south, east, and west; thus, allowing the division of the surface into four equal quadrants: northeast, southeast, northwest, and southwest. In the room where the experiments were carried out, there are visual cues around the tank, such as: figures fixed on the walls, window, and door, to assist the animals during the tests.

Figure 16:
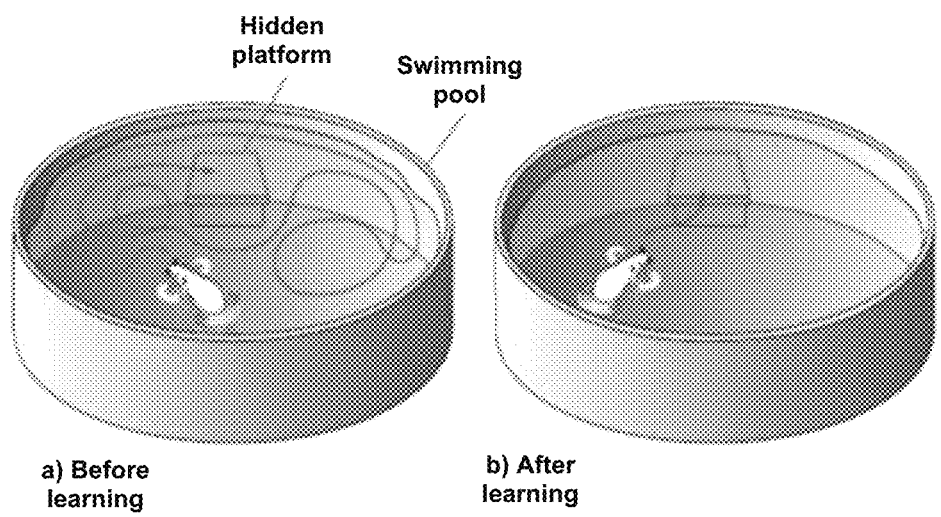
FIG. 16 shows the model used in the Morris water maze.
Figure 17:
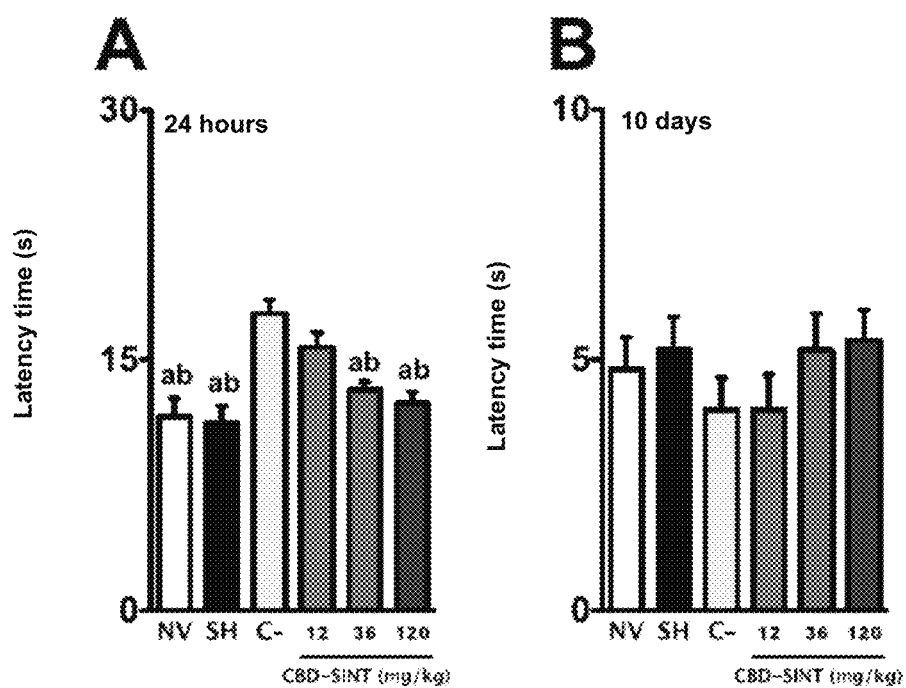
FIG. 17 shows the latency times to start the movements in the open field test after 24 hours and 10 days after MPTP administration.
Figure 18:
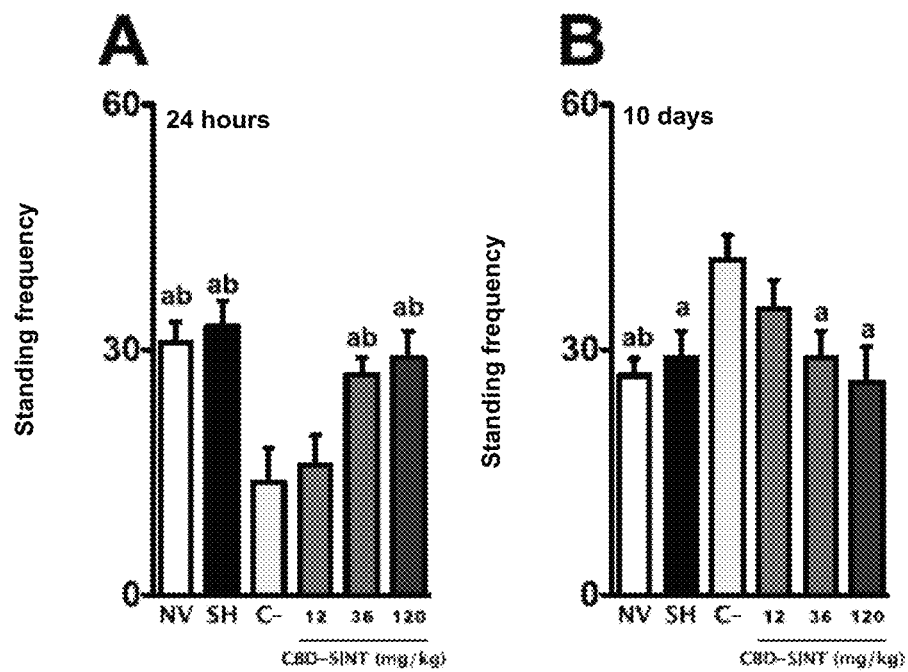
FIG. 18 shows the frequencies of lifting among all experimental groups treated with MPTP.
Figure 19:
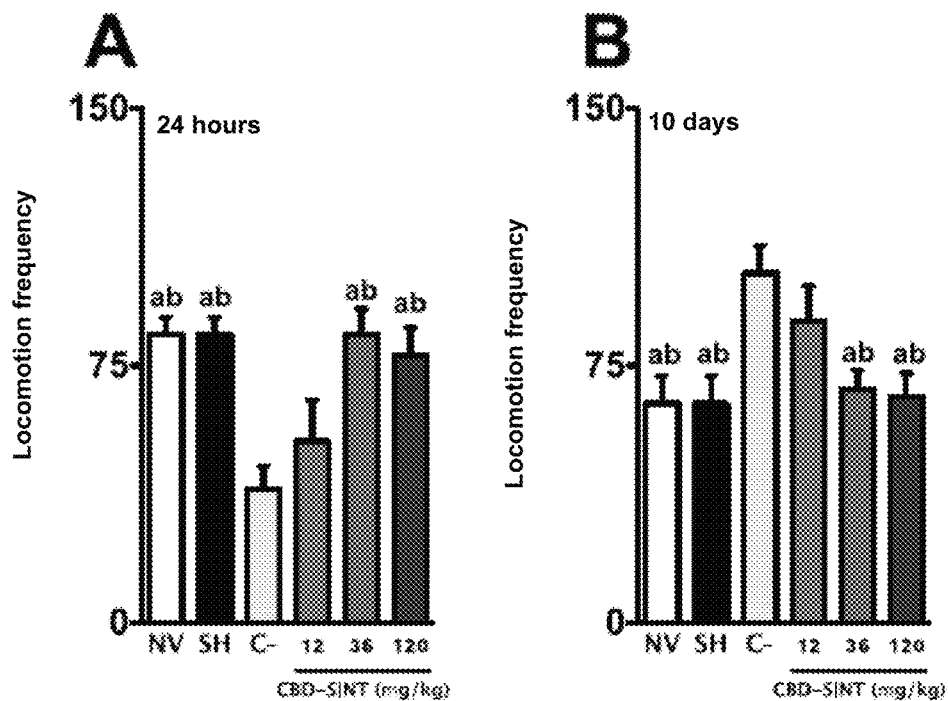
FIG. 19 shows the locomotion frequencies among all experimental groups treated with MPTP.
Figure 20:
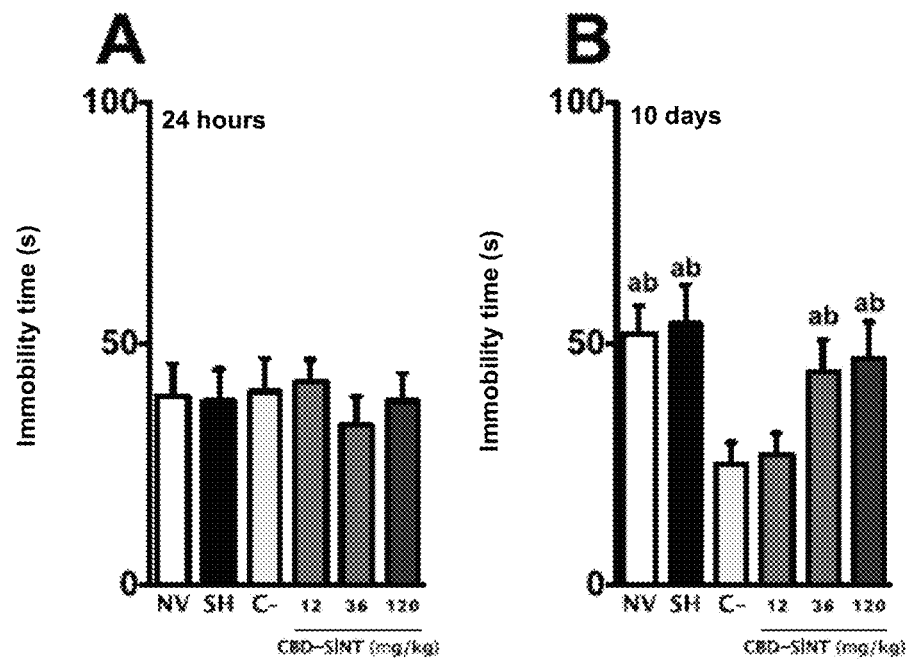
FIG. 20 shows the immobility time obtained from treatment with MPTP.

For the tests, a transparent acrylic platform (11×14×29 cm) was used with a sphere with the upper half painted in black and the lower white, 7 cm in diameter fixed on an acrylic platform (FIG. 16).

During the experiment, the platform was kept submerged at 2 cm below the water surface, while the sphere remained visible to the rats. On test days the platform with the sphere was fixed in one of the four quadrants: northeast, southeast, northwest and southwest, respectively, while the animal was released to swim until it found the platform in one of the four starting points: south, east, north and west, respectively. The animal should find the platform in a maximum time of 60 s. When the maximum time was reached, the animals were gently guided by the experimenter to the platform with the sphere (visual cue). After rats found the cue, they remained on the sphere for 20 s, after which time the animals were removed from the platform and placed for 30 s in the housing cage outside the water maze. During this period, the platform was changed positions by the experimenter.

The animals were subjected to the same procedure until the four starting points are completed. The starting and platform positions were planned so that the distal and proximal distances were alternated. The latency (time it takes the animals to find the platform) and the speed of the animals were quantified by the 2020 Plus Tracking System software.

c) Determination of Dopamine Levels and its Metabolites 3,4-Dihydroxyphenylacetic Acid (DOPAC) and Homovanilic Acid (HVA)

After the last set of experiments, the animals from the nigrostriatal treatment with MPTP and its respective controls were euthanized by decapitation. The levels of dopamine (DA) and its metabolites 3,4-dihydroxyphenylacetic acid (DOPAC) and homovanilic acid (HVA) were determined by high-performance liquid chromatography with an electrochemical detector (HPLC-ECD) according to Luo et al. (2009).

Briefly, the striatum was dissected, weighed, and homogenized in 0.2 M cold perchloric acid. The sample was then centrifuged twice at 14,000 g for 15 min at 4° C. The supernatant was collected and filtered through a 0.22 µm Millipore filter and injected into the HPLC system for analysis.

Regarding the neuroprotective effects of CBD-SINT on behavioral changes induced by the administration of MPTP, results were obtained considering three factors.

d) Effects of CBD-SINT on Locomotor Activity (MPTP)

The results showed 24 h after the infusion of MPTP, the negative control group (C−: MPTP+placebo) had a significant increase in latency for the beginning of movements. In fact, locomotor activity was found to be significantly reduced for this group compared to the naive and Sham groups, demonstrating the MPTP model in rats produced a reduction in animal activity as expected for the model.

The data show 24 h after the injury, the negative control group showed a significant decrease in the frequency of standing up in relation to the naive and Sham groups. At 10 days, the MPTP+placebo (C−) group exhibited a significant increase in the frequency of standing when compared to the naive or Sham groups.

After 24 hours, the negative control animals (C−: MPTP+placebo) showed a significant reduction in the frequency of locomotion, with values significantly lower than those found in rats from the naive or Sham groups.

On the other hand, the frequency of locomotion seen in animals of the negative control group 10 days after the administration of MPTP was quite different from that observed after 24 hours. If after 24 hours, locomotor activity was significantly reduced, after 10 days the results were quite different.

The immobility time showed 24 h after surgery the MPTP+placebo group did not statistically differ from any of the other experimental groups. On the other hand, at ten days, the negative control group had a significant decrease in immobility when compared to the naive and Sham groups.

Regarding the effect caused by CBD-SINT administration on animals, it was seen at doses of 36 mg/kg and 120 mg/kg, CBD-SINT showed similar values to animals in the naive or Sham group, in all the factors noted above, with a surprising effect on the latency time and frequency of standing factors, where a lower concentration had a more effective result compared to the effect of a CBD-FITO, that is, organic, in the same concentration (FIGS. 17-20).

The aforementioned data, together with the results obtained in this example, allows us to conjecture CBD-SINT has significant neuroprotective effects compared to this experimental model, opening perspectives for the use of these compounds on the control of the Parkinson's disease symptoms.

e) Effects of CBD-SINT on Memory (MPTP)

Figure 21:
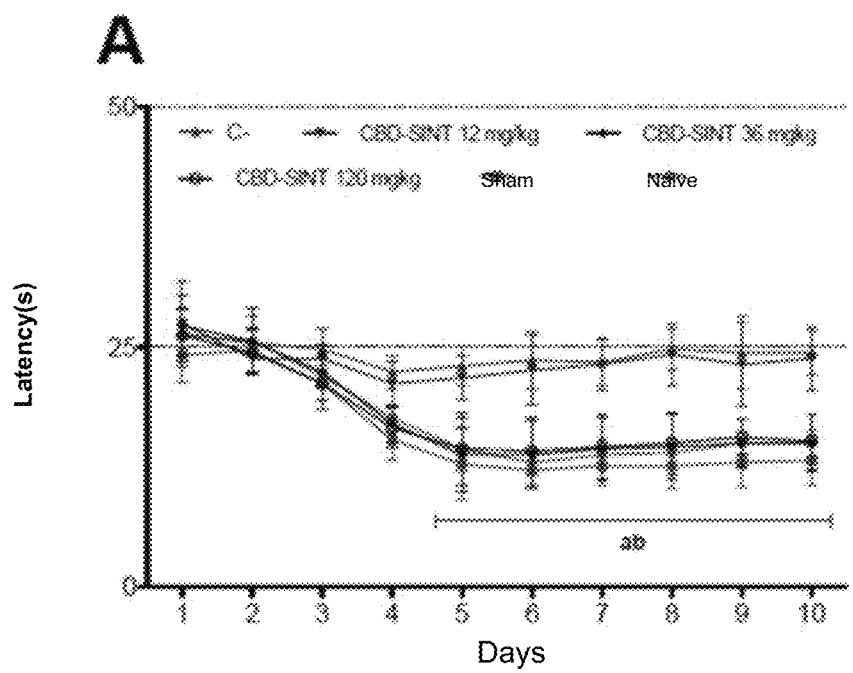
FIG. 21 shows the results obtained from the effect of CBD-SINT on memory with treatment with MPTP.

As shown in FIG. 21 (A and B), rats in the MPTP+placebo group (negative control; C−) showed a significant increase in the latency time to find the platform when compared to the naive or Sham group of animals. These changes started on the 5th day of training and lasted until the 10th day.

Treatment with CBD-SINT at 36 and 120 mg/kg doses prevented this deficit, maintaining latency times at values statistically similar to those of animals which did not receive MPTP, as seen in a CBD-FITO in same concentration.

f) Effects of CBD-SINT on Striatal Levels of Dopamine, DOPAC and AVM (MPTP)

Figure 22:
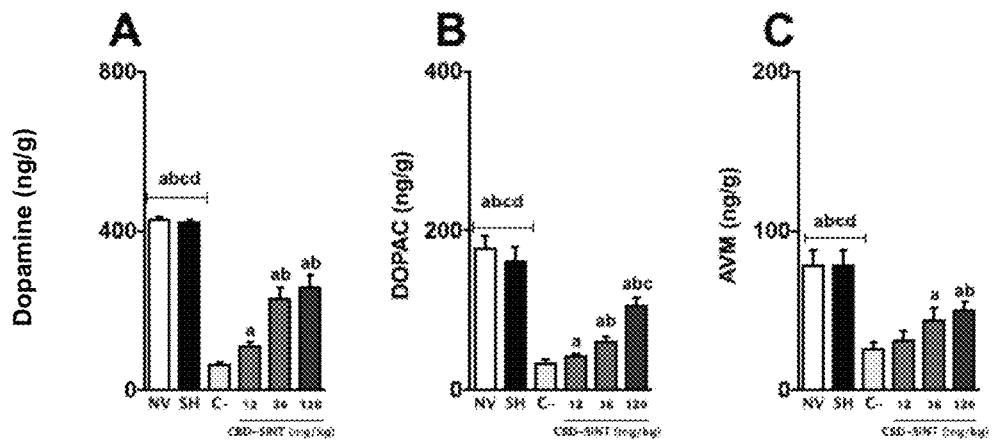
FIG. 22 shows the values found for the levels of dopamine, DOPAC and striatal AVM among the different experimental groups treated with MPTP.
Figure 23:
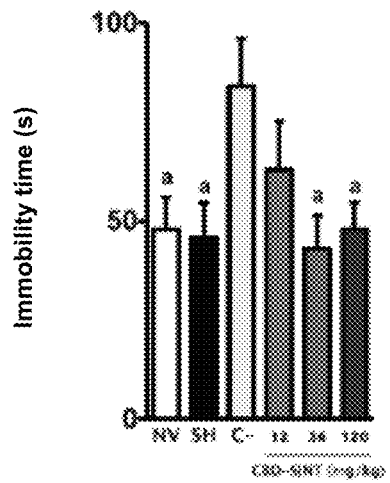
FIG. 23 shows the immobility time among all experimental groups treated with the 6-OHDA toxin.
Figure 24:
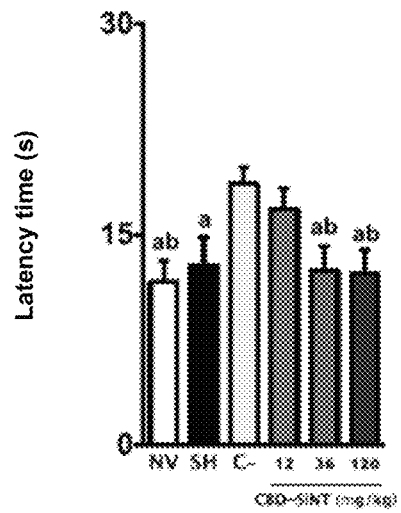
FIG. 24 shows the latency time to movement showed by animals treated with the 6-OHDA toxin.
Figure 25:
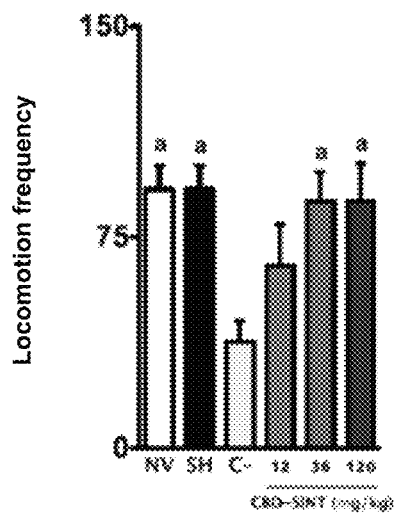
FIG. 25 shows the locomotion frequencies of the different experimental groups treated with the 6-OHDA toxin.
Figure 26:
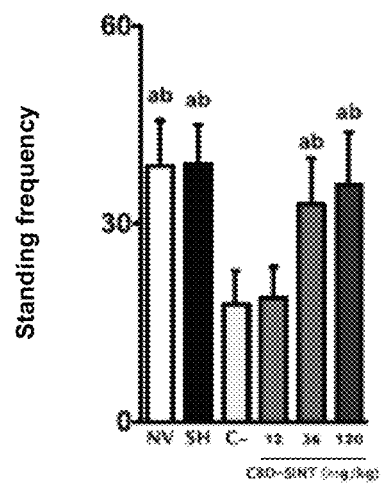
FIG. 26 shows the lifting frequencies of the different experimental groups treated with the 6-OHDA toxin.

The values found for the levels of dopamine, DOPAC and striatal AVM among the different experimental groups are shown in FIG. 22.

Intranigral administration of the MPTP toxin resulted in a significant reduction in the levels of all measured markers when compared with the naive or Sham groups. On the other hand, treatment with CBD-SI NT at a 12 mg/kg dose was able to significantly increase the levels of dopamine and DOPAC, while the 36 and 120 mg/kg doses increased the striatal concentration of all evaluated markers.

While the levels of all markers have risen after treatments with CBD-SINT, the values found were statistically lower than those identified in animals in the naive and Sham groups.

Regarding the effects of CBD-SINT on behavioral changes induced by the administration of 6-OHDA, the effects on three factors were considered.

d) Effects of CBD-SINT on Locomotor Activity (6-OHDA)

Data show that 35 days after the injury, the negative control group showed a significant increase in this parameter in relation to the naive and Sham groups.

Animals in the negative control group (C−: 6-OHDA+placebo) showed a significant increase in movement latency when compared to the naive or Sham groups.

Animals in the negative control group showed a significant reduction in locomotion after 35 days of administration of 6-OHDA.

Among all experimental groups, the animals of the negative control (C−: 6-OHDA+placebo) mg/kg have a frequency of standing significantly lower than the naive groups, Sham.

Regarding the effect caused by the CBD-SINT administration on animals, it was observed that at 36 mg/kg and 120 mg/kg doses, CBD-SINT showed similar values to animals in the naive or Sham group, in all the factors noted above, with a surprising effect on the immobility time factor (FIGS. 23-26).

h) Effects of CBD-SINT on Memory (6-OHDA)

Figure 27:
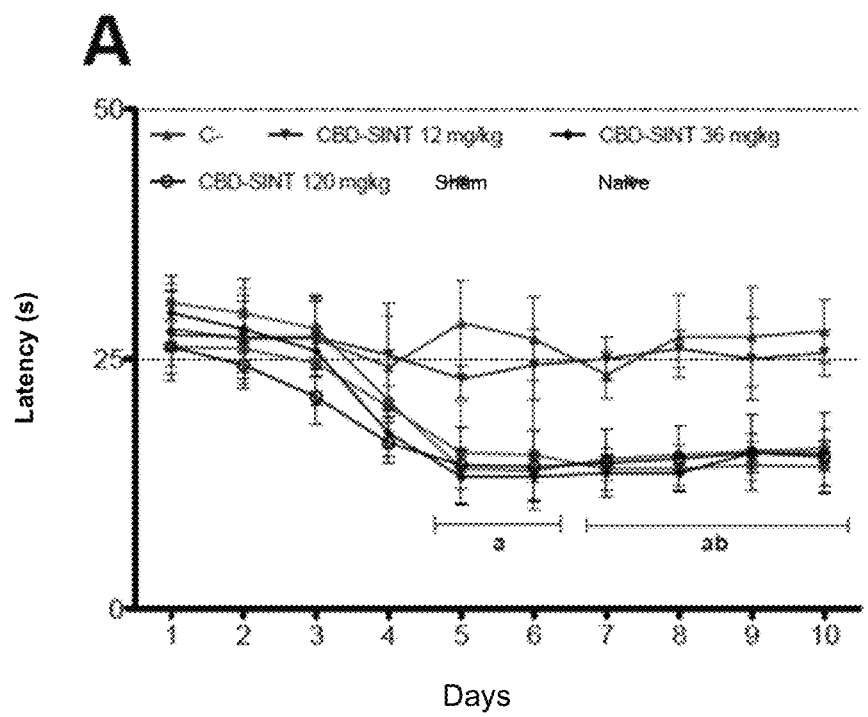
FIG. 27 shows the necessary latency time for the different experimental groups treated with 6-OHDA and its respective controls to find the platform in the Morris Water Labyrinth test.

FIG. 27 shows the necessary latency time for the different experimental groups treated with 6-OHDA and its respective controls to find the platform in the Morris Water Labyrinth test.

All animals in the negative control group (6-OHDA+placebo: C−) showed a significant increase in the latency time to find the safety platform, showing an important memory deficit from the 5th to the 10th test day.

Surprisingly, all groups treated with CBD-SINT at 36 or 120 mg/kg doses did not show this deficit, showing a latency period similar to animals in the naive or Sham groups.

The invention claimed is:

1. A method for neuroprotective action comprising the administration to a human or an animal of a pharmaceutical composition comprising Cannabidiol of synthetic origin, wherein said composition comprises up to 0.06% Cannabinol, up to 0.06% Delta-8-tetrahydrocannabinol, up to 0.06% Delta-9-tetrahydrocannabinol, up to 0.06% Cannabidiolic acid methyl ester, up to 0.06% Menthadienol, and up to 0.06% Methyl olivetolate.

2. The method of treatment according to claim 1, wherein the administration is at the dose of 100 to 1750 mg/day.

3. The method according to claim 2, wherein the dose is a single dose or doses divided throughout the day.

4. The method according to claim 1, wherein the neuroprotective action is for neurological disorders selected from the group consisting of refractory epilepsy, epilepsy, schizophrenia, sleep disorders, post-traumatic disorder, Alzheimer's disease, anxiety, depression, bipolar disorder, neuropathic pain, chronic pain relief, autism, chronic pain relief, and Parkinson's disease.

* * * * *